United States Patent
Chae et al.

(10) Patent No.: US 11,524,975 B2
(45) Date of Patent: Dec. 13, 2022

(54) AMPHIPHILIC COMPOUND HAVING DENDRONIC HYDROPHOBIC GROUP AND APPLICATION THEREOF

(71) Applicant: Industry-University Cooperation Foundation Hanyang University Erica Campus, Ansan-si (KR)

(72) Inventors: Pil Seok Chae, Ansan-si (KR); Aiman Sadaf, Ansan-si (KR)

(73) Assignee: Industry-University Cooperation Foundation Hanyang University Erica Campus, Yeonsu-gu (KR)

( * ) Notice: Subject to any disclaimer, the term of this patent is extended or adjusted under 35 U.S.C. 154(b) by 437 days.

(21) Appl. No.: 16/755,580

(22) PCT Filed: Feb. 28, 2018

(86) PCT No.: PCT/KR2018/002459
§ 371 (c)(1),
(2) Date: Apr. 12, 2020

(87) PCT Pub. No.: WO2019/074171
PCT Pub. Date: Apr. 18, 2019

(65) Prior Publication Data
US 2020/0247836 A1 Aug. 6, 2020

(30) Foreign Application Priority Data
Oct. 11, 2017 (KR) .................. 10-2017-0130038

(51) Int. Cl.
C07H 3/04 (2006.01)
C07H 3/06 (2006.01)
C07H 15/08 (2006.01)
C07K 1/14 (2006.01)
G01N 33/68 (2006.01)

(52) U.S. Cl.
CPC ............... C07H 15/08 (2013.01); C07H 3/04 (2013.01); C07H 3/06 (2013.01); C07K 1/14 (2013.01); G01N 33/6842 (2013.01)

(58) Field of Classification Search
None
See application file for complete search history.

(56) References Cited

U.S. PATENT DOCUMENTS

| | | | |
|---|---|---|---|
| 8,877,906 B2 * | 11/2014 | Gellman ............... | C07H 15/02 536/17.2 |
| 10,781,229 B2 * | 9/2020 | Chae ................... | G01N 33/68 |
| 2009/0270598 A1 | 10/2009 | Gellman et al. | |
| 2019/0077822 A1 | 3/2019 | Chae et al. | |
| 2019/0284221 A1 | 9/2019 | Chae et al. | |

FOREIGN PATENT DOCUMENTS

| | | |
|---|---|---|
| KR | 10-2017-0030261 | 3/2017 |
| KR | 10-2017-0070400 | 6/2017 |
| WO | WO 2019/074171 | 4/2019 |

OTHER PUBLICATIONS

Grounds of Reasons for Rejection dated Jun. 18, 2019 From the Korean Intellectual Property Office Re. Application No. 10-2018-0024459. (7 Pages).
International Search Report and the Written Opinion dated Jul. 11, 2018 From the International Searching Authority Re. Application No. PCT/KR2018/002459 and its Translation of Search Report Into English. (18 Pages).
Bae et al. "Tandem Neopentyl Glycol Maltosides (TNMs) for Membrane Protein Stabilisation", Chemical Communications. 52(81): 12104-12107, Oct. 4, 2016.
Cho et al. "Synthesis and Self-Assembly of Amphiphilic Dendrimers Based on Aliphatic Polyether-Type Dendritic Cores", Macromolecules, 37(11): 4227-4232, Published on Web May 5, 2004.
Ehsan et al. "Highly Branched Pentasaccharide-Bearing Amphiphiles for Membrane Protein Studies", Journal of the American Chemical Society, 138(11): 3789-3796, Published Online Mar. 11, 2016.
Newstead et al. "Insights Into Outer Membrane Protein Crystallization", Molecular Membrane Biology, 25(8): 631-638, Dec. 2008.
Newstead et al. "Rationalizing Alpha-Helical Membrane Protein Crystallization", Protein Science, 17(3): 466-472, Published Online Jan. 24, 2008.
Sadaf et al. "Dendronic Trimaltoside Amphiphiles (DTMs) for Membrane Protein Study", Chemical Science, 8(12): 8315-8324, Published Online Oct. 25, 2017.

* cited by examiner

*Primary Examiner* — Traviss C McIntosh, III

(57) ABSTRACT

The present invention relates to an amphiphilic compound having a dendronic hydrophobic group, a method for preparing the same, and a method for extraction, solubilization, stabilization, or crystallization of a membrane protein by using the same. The use of the compound according to the present invention leads to an excellent membrane protein solubilization effect and a stable storage of a membrane protein in an aqueous solution for a long time, and thus can be utilized for functional analysis and structural analysis of the membrane protein. Especially, the amphiphilic compound having a dendronic hydrophobic group showed very remarkable characteristics in the visualization of protein composites through an electronic microscope. The membrane protein structural and functional analysis is one of the fields of greatest interest in current biology and chemistry, and more than half of the new drugs that are currently being developed are targeted at membrane proteins, and thus the amphiphilic compound of the present invention can be applied to membrane protein structure studies closely related to the development of new drugs.

18 Claims, 9 Drawing Sheets

[FIG 1]
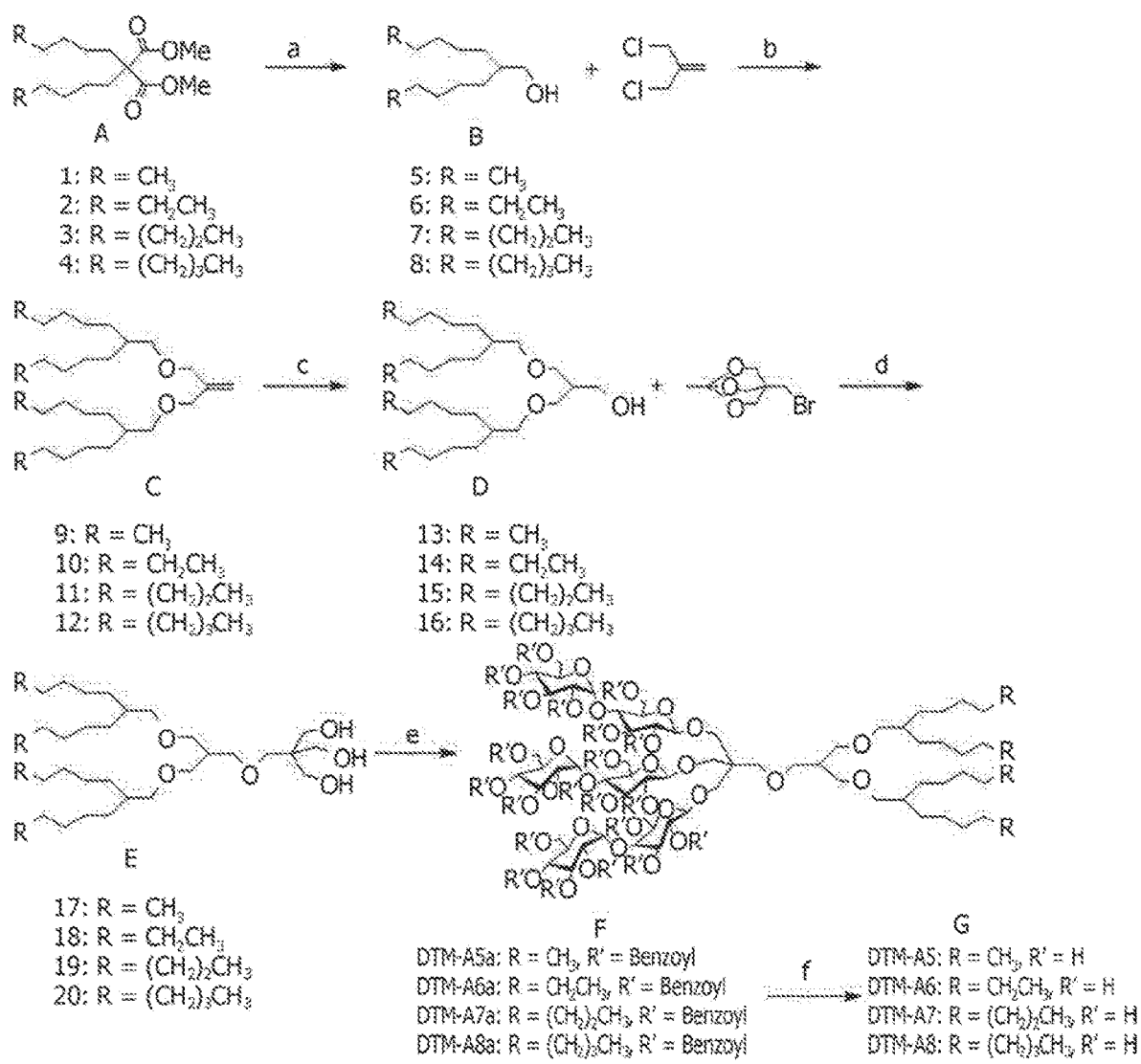

[FIG 2]
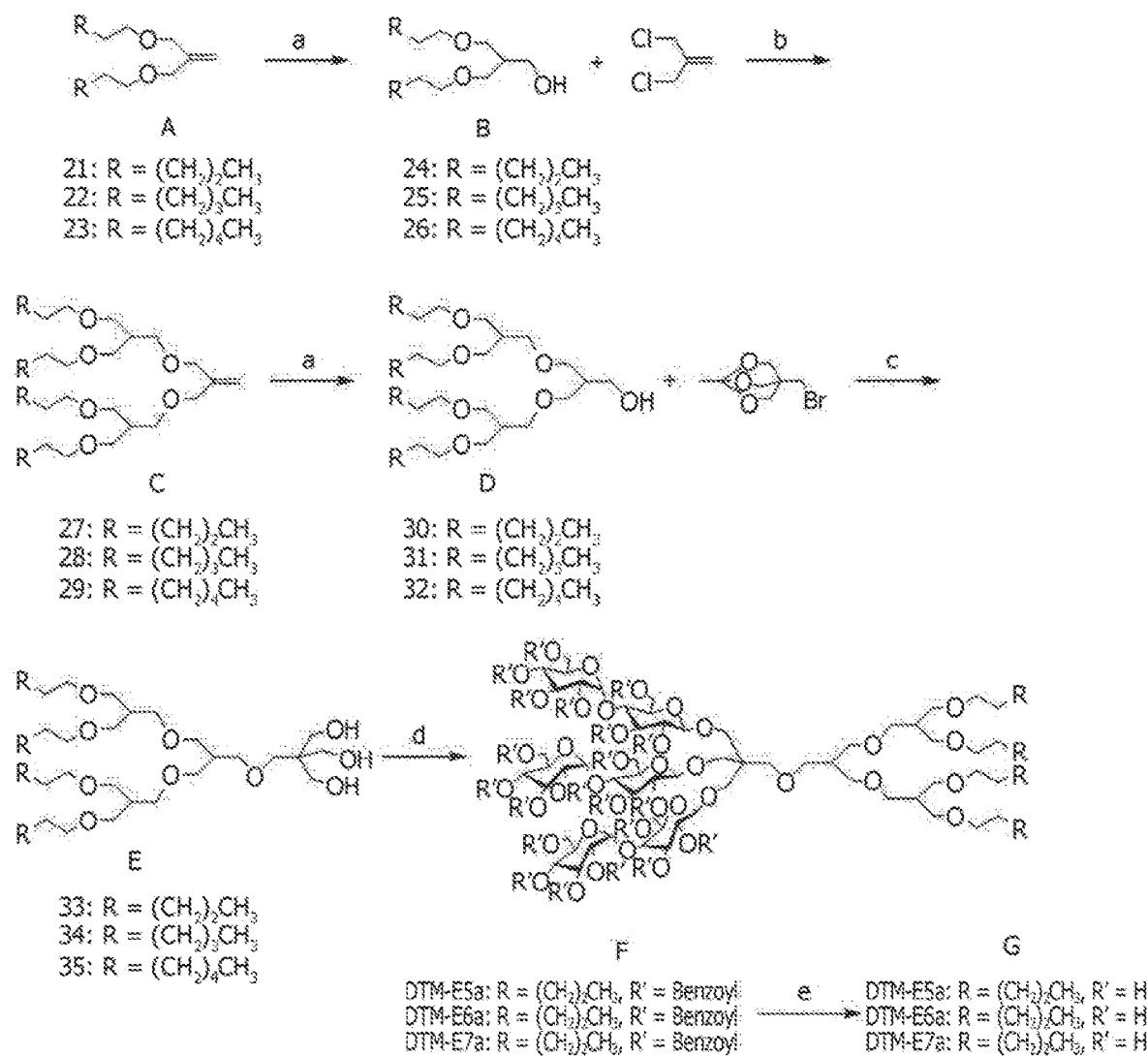

[FIG 3]
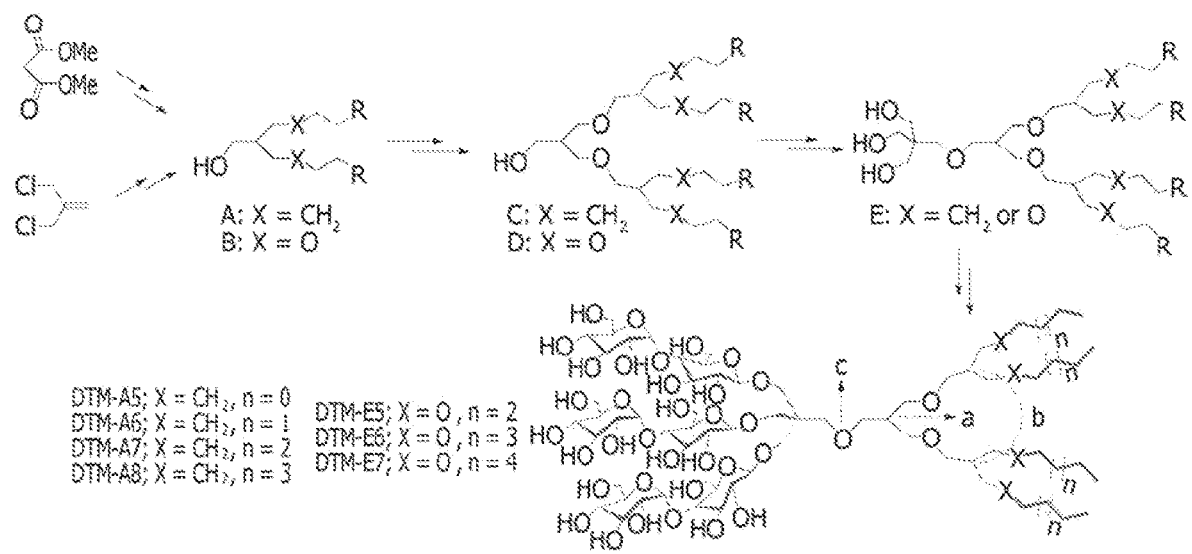
[FIG 4]
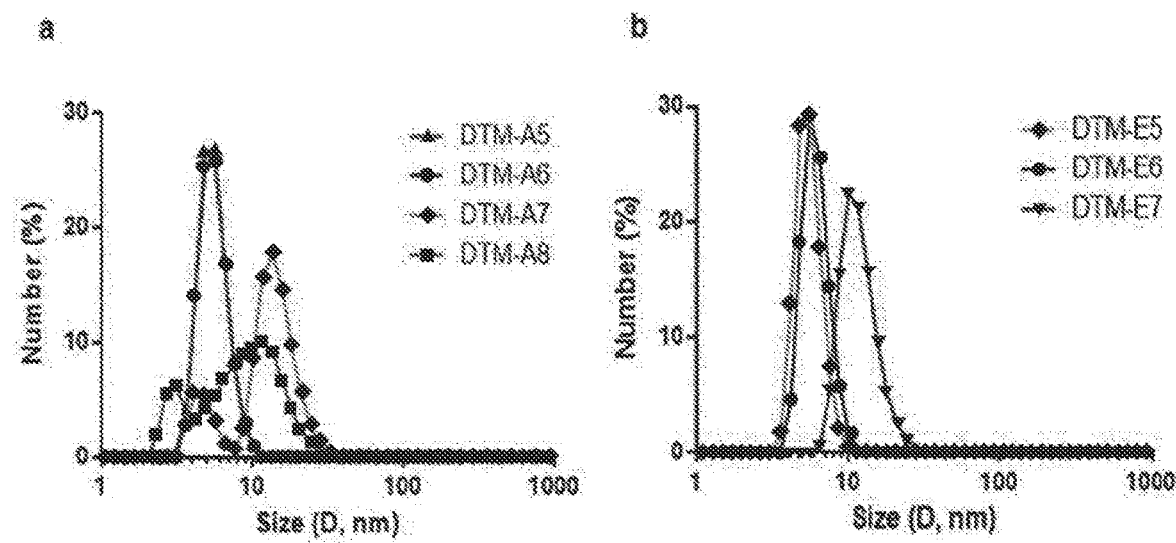

[FIG 5]
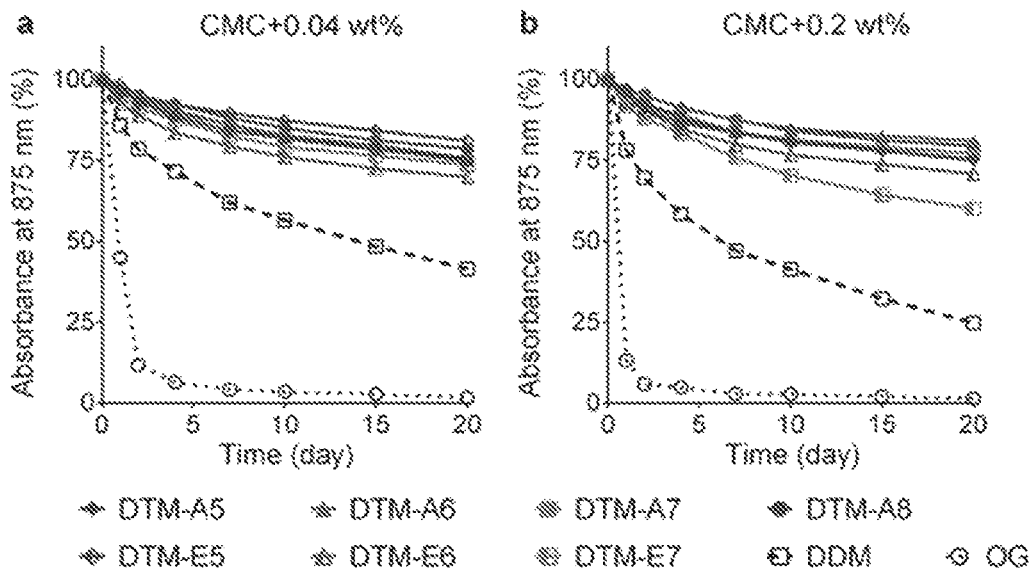
[FIG 6]
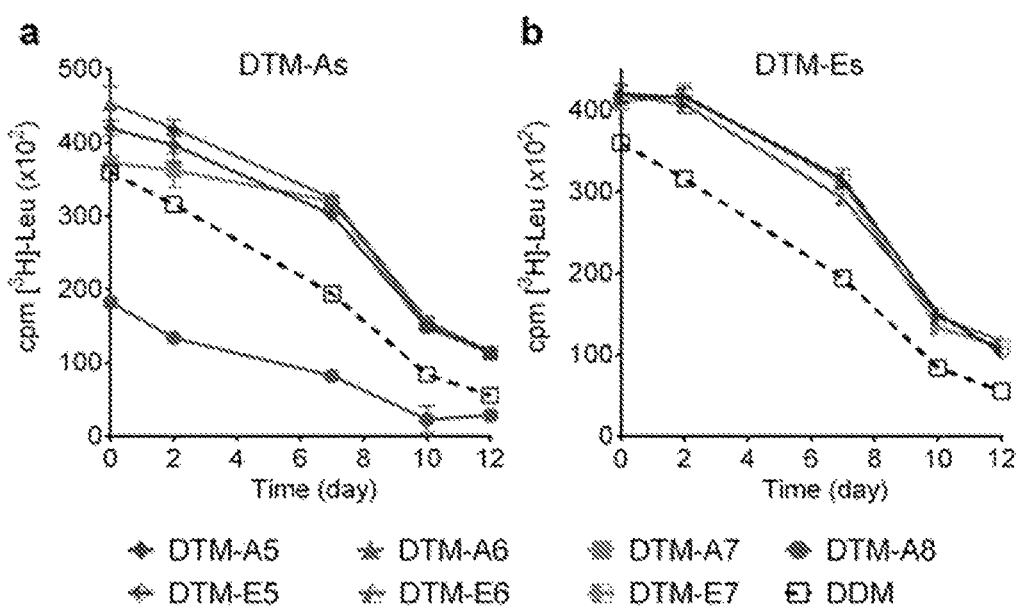

[FIG 7]
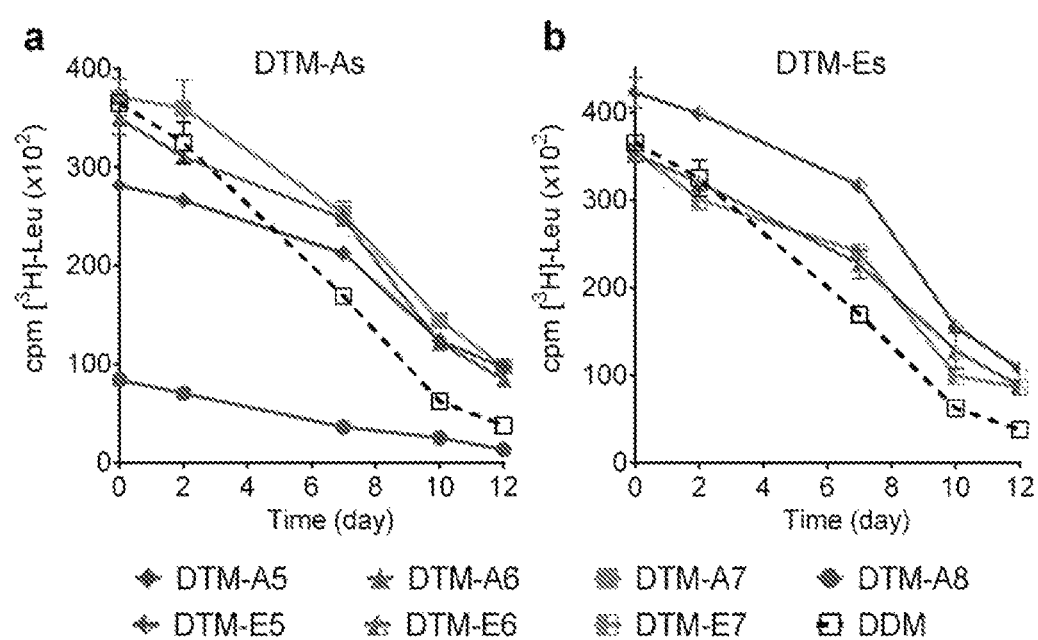

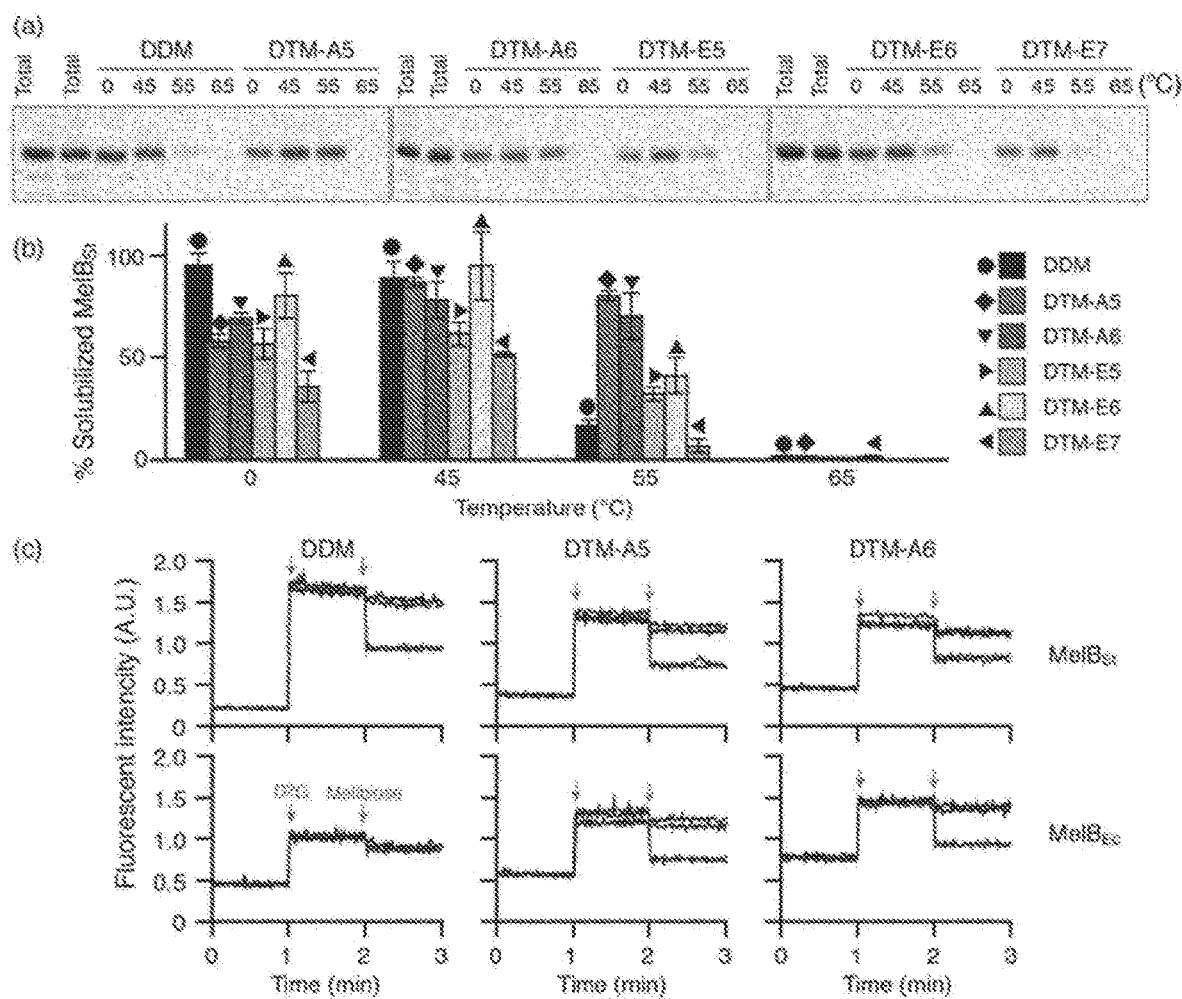
[FIG 8]

[FIG 9]
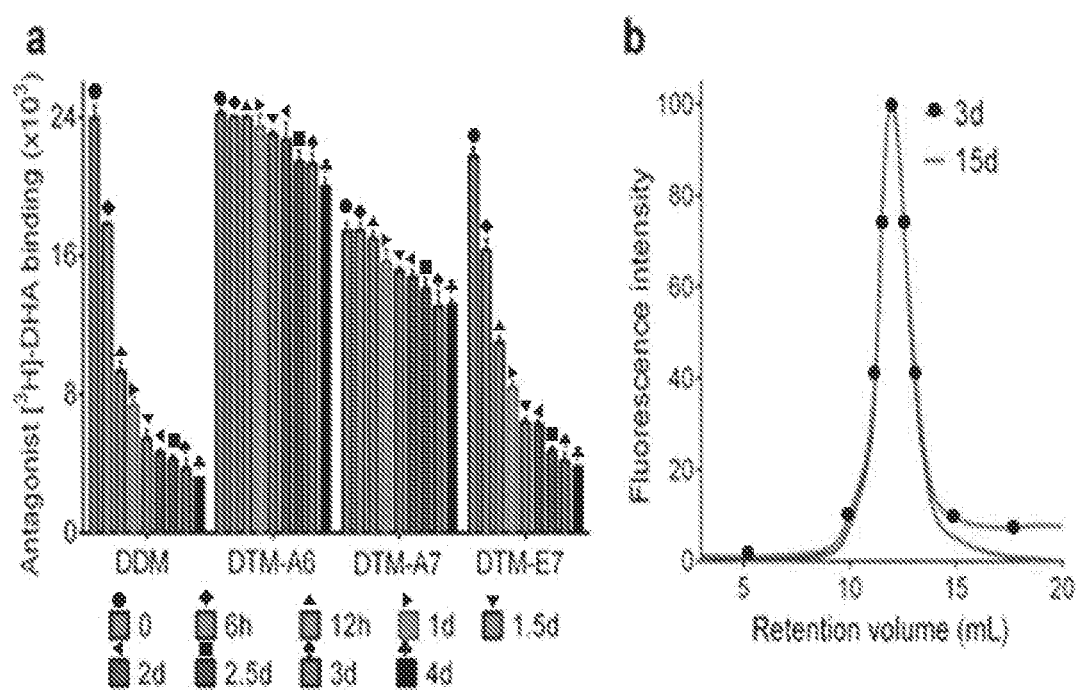

[FIG 10]
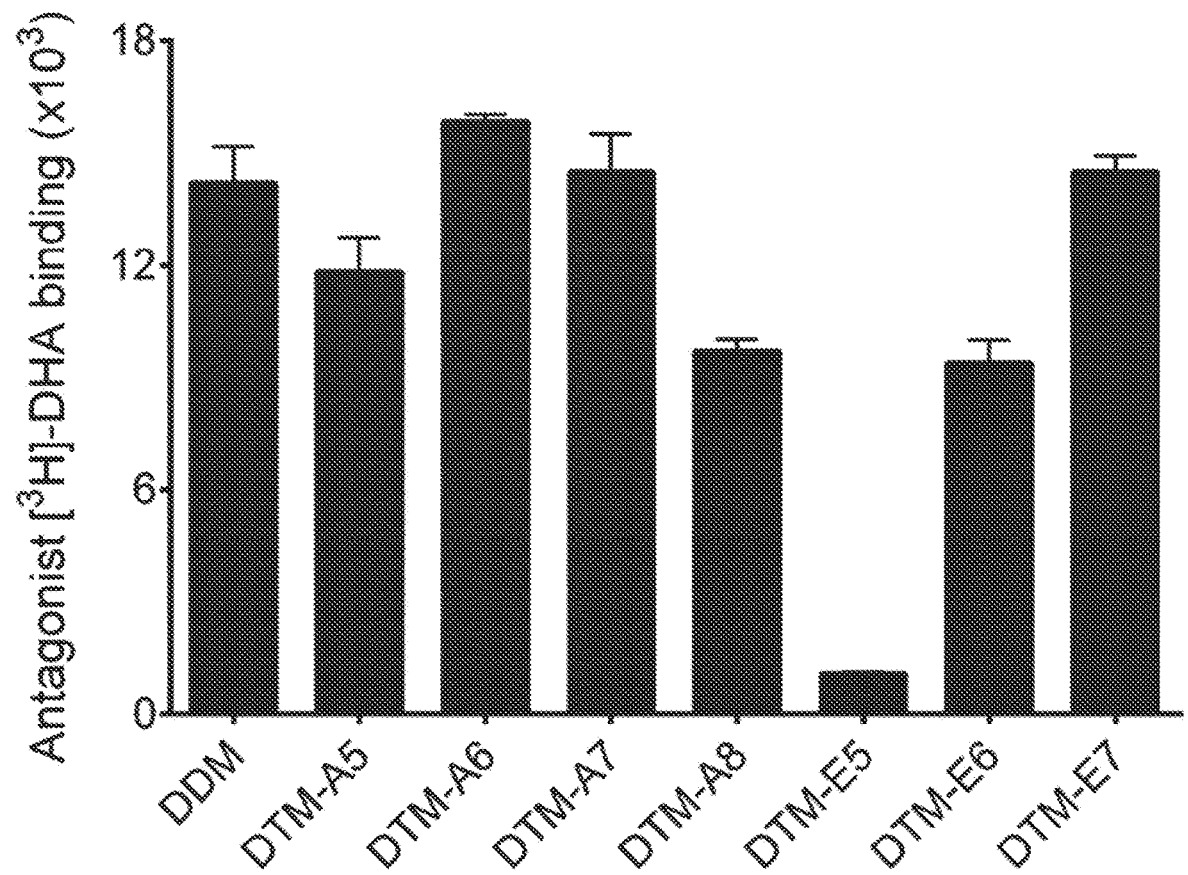

[FIG 11]
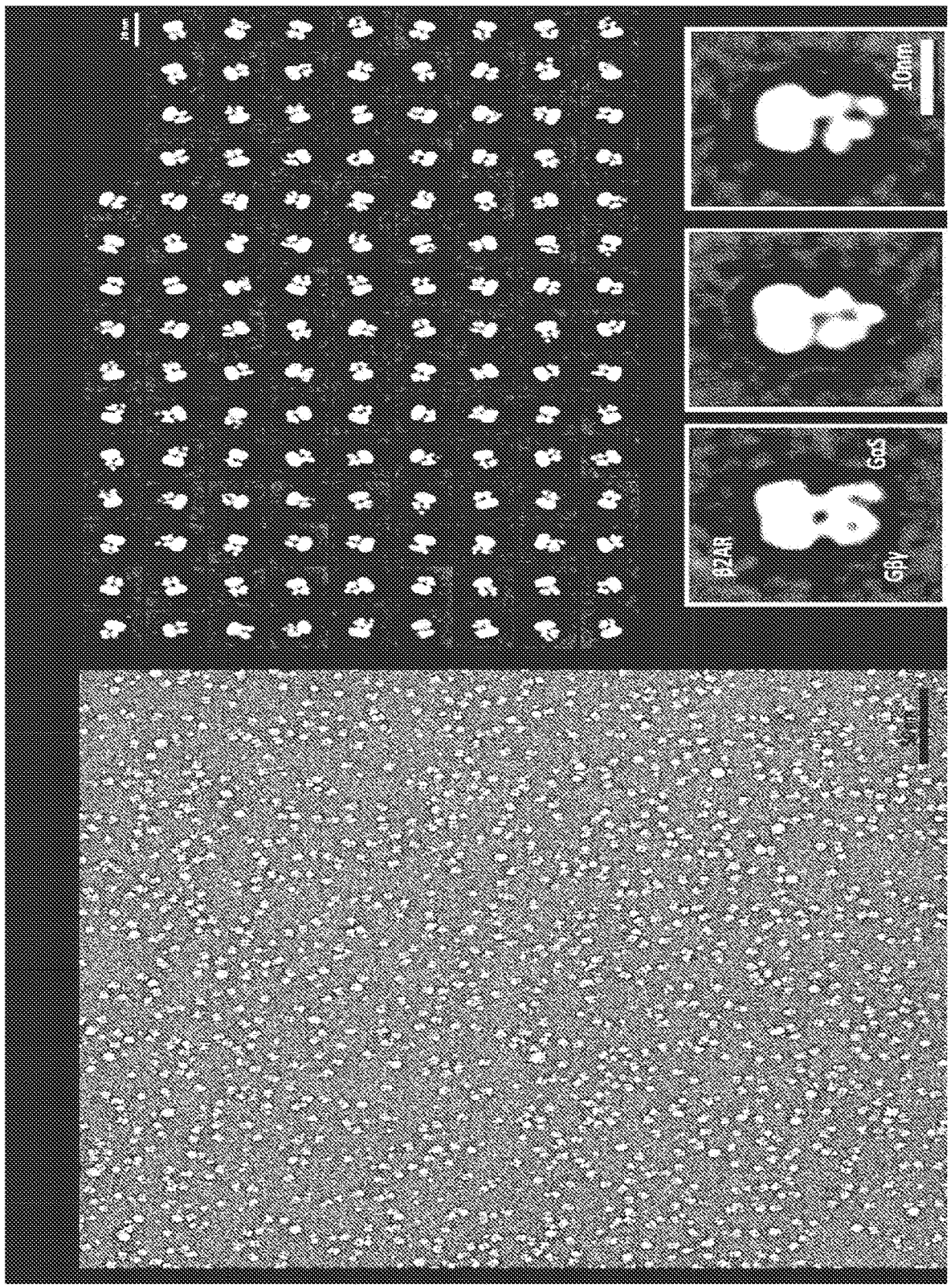

AMPHIPHILIC COMPOUND HAVING DENDRONIC HYDROPHOBIC GROUP AND APPLICATION THEREOF

RELATED APPLICATIONS

This application is a National Phase of PCT Patent Application No. PCT/KR2018/002459 having International filing date of Feb. 28, 2018, which claims the benefit of priority of Korean Patent Application No. 10-2017-0130038, filed on Oct. 11, 2017. The contents of the above applications are all incorporated by reference as if fully set forth herein in their entirety.

FIELD AND BACKGROUND OF THE INVENTION

The present invention relates to a novel amphiphilic compound having a dendronic hydrophobic group and a method of extracting, solubilizing, stabilizing, crystallizing or analyzing a membrane protein using the same.

Membrane proteins play a pivotal role in a biological system. Since these bio-macromolecules include hydrophilic and hydrophobic moieties, amphiphilic molecules are required for extraction of membrane proteins from a lipid environment, and solubilization and stabilization of the membrane proteins in an aqueous solution.

To analyze the structure of a membrane protein, it is necessary to obtain a high quality of membrane protein crystals, and to this end, structural stability of the membrane protein in an aqueous solution should be preceded. Although there are 100 or more types of conventional amphiphilic molecules that have been used in membrane protein studies, only five of them are actively used for the membrane protein structure studies. These five types of amphoteric molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (Non-Patent Document 1, Non-Patent Document 2). However, since a lot of membrane proteins surrounded by these molecules are changed in structure, for example, easily denatured or aggregated, leading to rapid loss of their functions, there are a lot of limits on the research on the function and structure of a membrane protein using these molecules. This is because conventional molecules do not exhibit sufficiently diverse properties due to their simple chemical structures.

To analyze the structure of a membrane protein, maintenance of the structural stability of a membrane protein in an aqueous solution is important, and since there are still many unknown types of membrane proteins, and they have diverse structural properties, the number of membrane proteins that can be identified with the conventionally used amphiphilic molecules has been limited.

The inventors developed an amphiphilic compound having a novel structure, which promotes membrane protein crystallization, by introducing a hydrophobic group having a dendronic structure with four hydrophobic chains extending radially at one spot, and thus the present invention was completed.

(Non-Patent Document 1) S. Newstead et al., *Protein Sci.* 17 (2008) 466-472.

(Non-Patent Document 2) S. Newstead et al., *Mol. Membr. Biol.* 25 (2008) 631-638.

SUMMARY OF THE INVENTION

The present invention is directed to providing a compound represented by Formula 1.

The present invention is also directed to providing a composition for extracting, solubilizing, stabilizing, crystallizing or analyzing a membrane protein containing the compound.

The present invention is also directed to providing a method of preparing the compound.

The present invention is also directed to providing a method of extracting, solubilizing, stabilizing, crystallizing or analyzing a membrane protein using the compound.

One aspect of the present invention provides a compound represented by Formula 1 below:

[Formula 1]

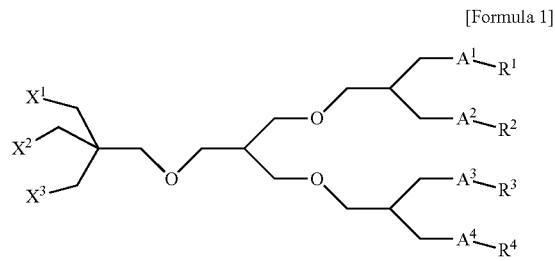

In Formula 1, $R^1$ to $R^4$ may be each independently a substituted or unsubstituted $C_1$-$C_{15}$ alkyl group, a substituted or unsubstituted $C_1$-$C_{15}$ cycloalkyl group, or a substituted or unsubstituted $C_1$-$C_{15}$ aryl group;

$A^1$ to $A^4$ may be each independently —$CH_2$—, oxygen (O) or sulfur (S); and $X^1$ to $X^3$ may be each independently an oxygen-linked saccharide.

The term "saccharide" used herein refers to a compound that has a relatively small molecule, compared with other carbohydrates, is dissolved in water and has a sweet taste. Saccharides are classified into monosaccharides, disaccharides and polysaccharides according to the number of molecules constituting a saccharide.

The saccharide used in the embodiment may be a monosaccharide or disaccharide, preferably glucose or maltose, and more preferably, maltose, but the present invention is not limited thereto.

The saccharide may act as a hydrophilic group. As three saccharides, which are hydrophilic groups, are connected in parallel to not only increase the size of the hydrophilic groups but also minimize the increase in length, the size of a complex formed with the compound according to one embodiment of the present invention and a membrane protein becomes smaller. When the complex formed with the compound and a membrane protein is small, a high-quality membrane protein crystal may be obtained (G. G. Prive, *Methods* 2007, 41, 388-397). Particularly, an amphiphilic molecule having a small hydrophilic group such as a glucoside may have an excellent effect on membrane protein crystallization.

In addition, $R^1$ to $R^4$ may act as a hydrophobic group. In the compound according to one embodiment of the present invention, to achieve the optimization of a hydrophile-lipophile balance, alkyl groups with different lengths were introduced as hydrophobic groups.

In the compound according to one embodiment of the present invention, the hydrophobic groups and the hydrophilic groups may be connected by ether bonds. That is, a linker was introduced to maintain rigidity at the center of the molecule and sufficiently ensure the flexibility of the alkyl chain.

In addition, the compound of the present invention has a hydrophobic group with a dendritic structure, wherein the dendronic structure is being used in various fields including drug delivery, biochemical sensors, and fluorescence imaging, but has not been implemented in an amphiphilic compound structure for membrane protein studies. This is because it is difficult to synthesize an amphiphilic dendronic structure having tail structures at both ends. In addition, there is a strict limit to the length of a hydrophobic alkyl chain of the amphiphilic compound, which may be overcome through the introduction of numerous alkyl chains to a dendronic structure. Moreover, while an amide or amine group is mainly used as a functional group that synthesizes a dendronic structure, these functional groups cannot favorably interact with a target membrane protein due to high polarity and rigidity.

Therefore, to solve the above-mentioned problem, the compound of the present invention corresponds to an amphiphilic compound including a hydrophobic group with a dendronic structure, which is effective in membrane protein analysis.

Specifically, $R^1$ to $R^4$ may be substituted or unsubstituted $C_1$-$C_{10}$ alkyl groups; $R^1$ to $R^4$ may be identical; $A^1$ to $A^4$ may be oxygen (O) or sulfur (S); and $X^1$ to $X^3$ may be oxygen-linked glucose or maltose.

In addition, $R^1$ to $R^4$ may be substituted or unsubstituted $C_1$-$C_{10}$ alkyl groups; $R^1$ to $R^4$ may be identical; $A^1$ to $A^4$ may be —$CH_2$—; and $X^1$ to $X^3$ may be oxygen-linked glucose or maltose.

In one embodiment of the present invention, compounds in which $R^1$ to $R^4$ are $C_1$-$C_{10}$ unsubstituted alkyl groups; $R^1$ to $R^4$ are identical; $A^1$ to $A^4$ are —$CH_2$—, oxygen (O) or sulfur (S); and $X^1$ to $X^3$ are oxygen-linked maltoses are named "dendronic trimaltosides (DTMs)."

More specifically, in one embodiment of the present invention, a compound in which $R^1$ to $R^4$ may be $C_3$ alkyl groups; $R^1$ to $R^4$ may be identical; $A^1$ to $A^4$ may be —$CH_2$—; and $X^1$ to $X^3$ may be oxygen-linked maltoses is named "DTM-A5," which is represented by Formula 2 below.

[Formula 2]

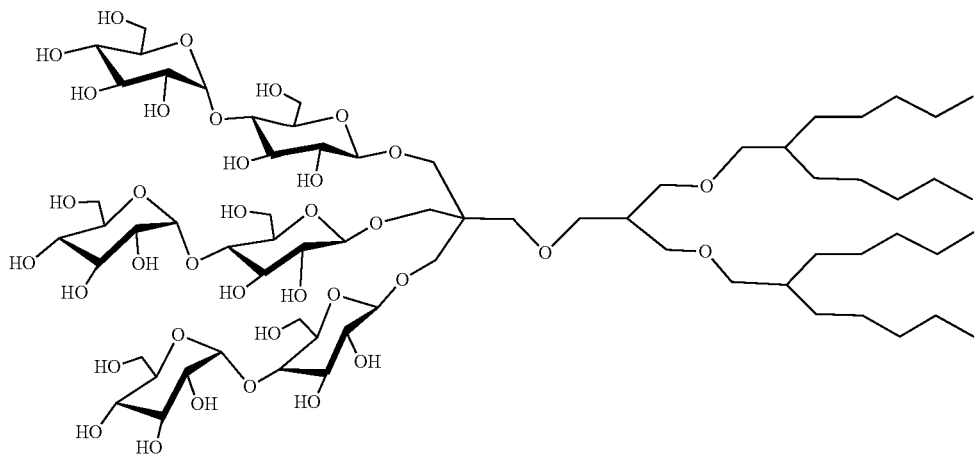

More specifically, in one embodiment of the present invention, a compound in which $R^1$ to $R^4$ may be $C_4$ alkyl groups; $R^1$ to $R^4$ may be identical; $A^1$ to $A^4$ may be —$CH_2$—; and $X^1$ to $X^3$ may be oxygen-linked maltoses is named "DTM-A6," which is represented by Formula 3 below.

[Formula 3]

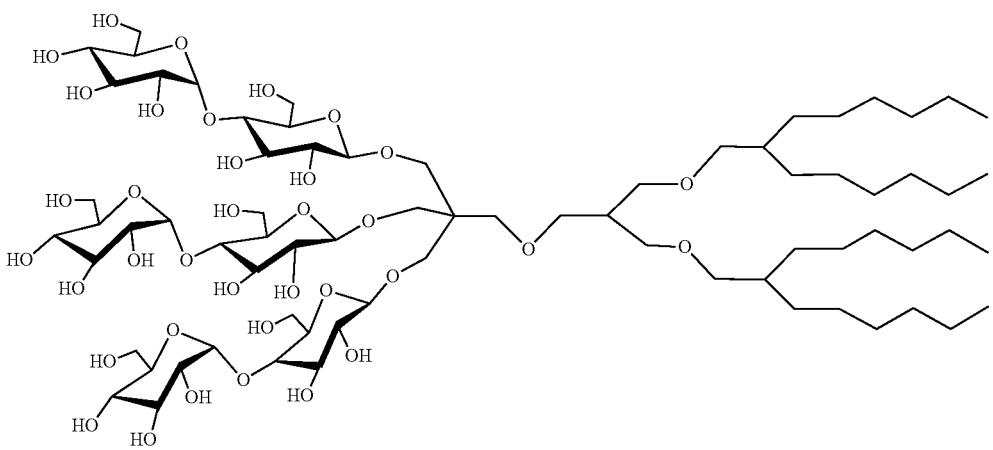

More specifically, in one embodiment of the present invention, a compound in which $R^1$ to $R^4$ may be $C_5$ alkyl groups; $R^1$ to $R^4$ may be identical; $A^1$ to $A^4$ may be —$CH_2$—; and $X^1$ to $X^3$ may be oxygen-linked maltoses is named "DTM-A7," which is represented by Formula 4 below.

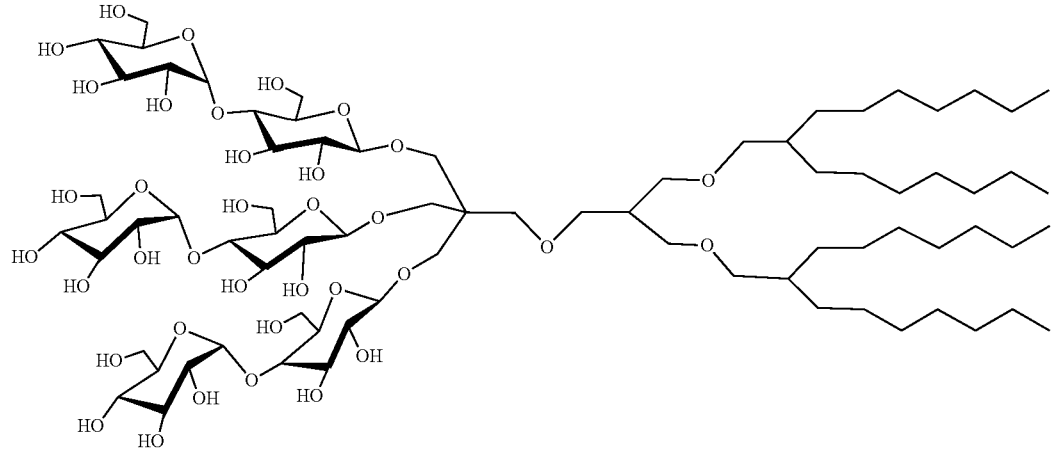

[Formula 4]

More specifically, in one embodiment of the present invention, a compound in which $R^1$ to $R^4$ may be $C_6$ alkyl groups; $R^1$ to $R^4$ may be identical; $A^1$ to $A^4$ may be —$CH_2$—; and $X^1$ to $X^3$ may be oxygen-linked maltoses is named "DTM-A8," which is represented by Formula 5 below.

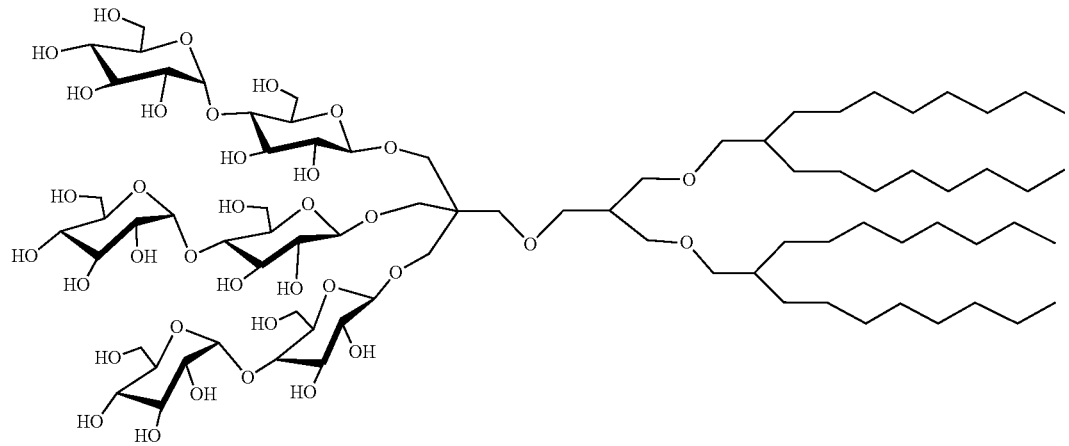

[Formula 5]

More specifically, in one embodiment of the present invention, a compound in which $R^1$ to $R^4$ may be $C_5$ alkyl groups; $R^1$ to $R^4$ may be identical; $A^1$ to $A^4$ may be oxygens (O); and $X^1$ to $X^3$ may be oxygen-linked maltoses is named "DTM-E5," which is represented by Formula 6 below.

[Formula 6]

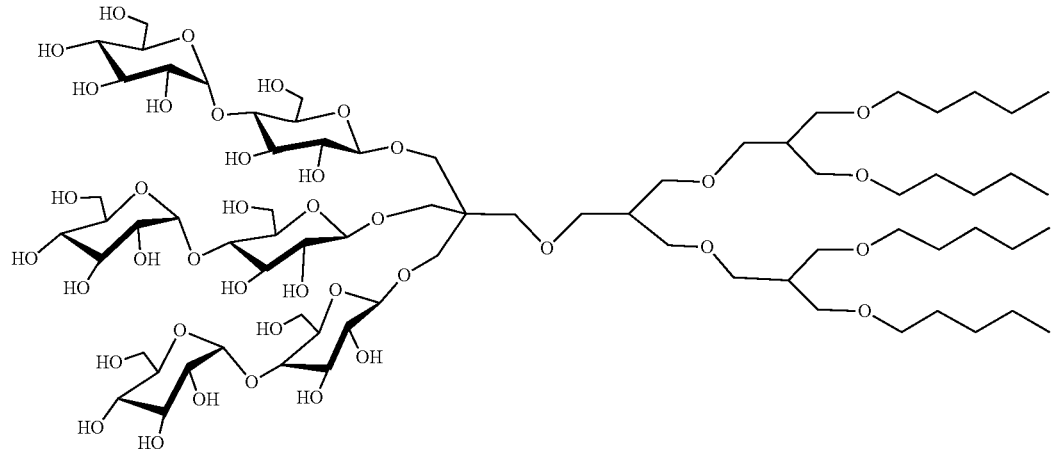

More specifically, in one embodiment of the present invention, a compound in which $R^1$ to $R^4$ may be $C_6$ alkyl groups; $R^1$ to $R^4$ may be identical; $A^1$ to $A^4$ may be oxygens (O); and $X^1$ to $X^3$ may be oxygen-linked maltoses is named "DTM-E6," which is represented by Formula 7 below.

[Formula 7]

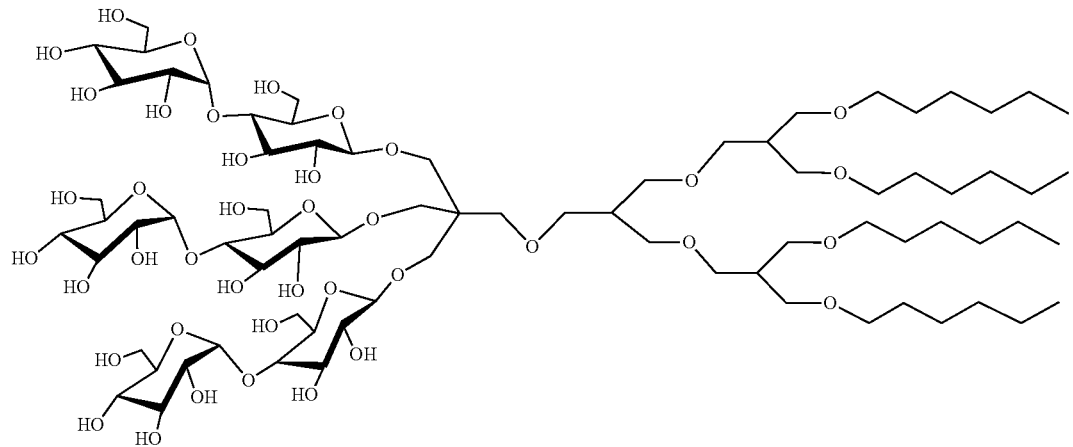

More specifically, in one embodiment of the present invention, a compound in which $R^1$ to $R^4$ may be $C_7$ alkyl groups; $R^1$ to $R^4$ may be identical; $A^1$ to $A^4$ may be oxygens (O); and $X^1$ to $X^3$ may be oxygen-linked maltoses is named "DTM-E7," which is represented by Formula 8 below.

The compound may be prepared in the form of a micelle, liposome, emulsion or nanoparticle, but the present invention is not limited thereto.

The micelle may have a radius of 2.0 to 60.0 nm, preferably 3.0 to 40.0 nm, and more preferably, micelles

[Formula 8]

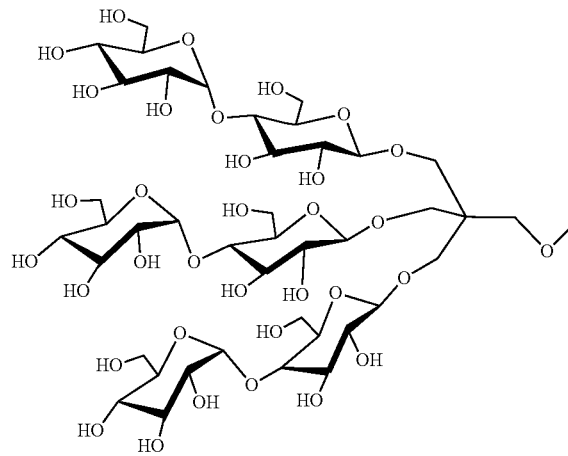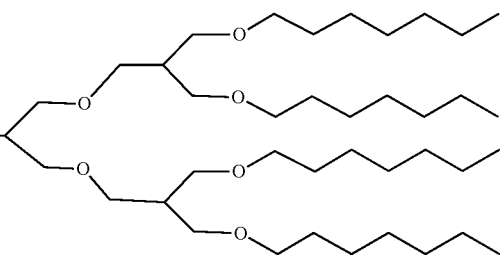

A compound according to another embodiment of the present invention may be an amphiphilic molecule for extracting, solubilizing, stabilizing, crystallizing or analyzing a membrane protein, but the present invention is not limited thereto.

The term "amphiphilic molecule" used herein refers to a molecule displaying the properties of polar and non-polar solvents because one molecule includes both of a hydrophobic group and a hydrophilic group. Phospholipid molecules present in a surfactant or cell membrane are molecules having a hydrophilic group at one end and a hydrophobic group at the other end, and are amphiphilic and form micelles or liposomes in an aqueous solution. Since the hydrophilic group has polarity, but the non-polar group is also present, the amphiphilic molecule is not well dissolved in water.

However, when a concentration reaches a critical micelle concentration (CMC) or higher, due to a hydrophobic interaction, a micelle in which hydrophobic groups gather together, and hydrophilic groups are placed on its surface is produced, and thus solubility in water greatly increases.

A method of measuring CMC is not particularly limited, and may be a method widely known in the art, for example, fluorescent staining using diphenylhexatriene (DPH).

The compound according to one embodiment of the present invention may have a CMC in an aqueous solution of 0.0001 mM to 1 mM, preferably, 0.0001 mM to 0.01 mM, and more preferably, 0.003 mM to 0.04 mM, but the present invention is not limited thereto.

DDM, which has been mainly used in conventional membrane protein studies, has a CMC of 0.17 mM, and DTMs of the embodiment have much smaller CMC values than DDM. Therefore, since DTMs easily form micelles even at a small amount, membrane proteins may be effectively studied and analyzed with a small amount, confirming that DTMs are advantageous over DDM.

Another aspect of the present invention provides a composition for extracting, solubilizing, stabilizing, crystallizing or analyzing a membrane protein, which includes the compound.

formed of DTMs according to embodiments of the present invention may have a radius of 3.0 to 35.0 nm, but the present invention is not limited thereto.

A method of measuring the radius of a micelle is not particularly limited, but may be a method well known in the art, for example, dynamic light scattering (DLS).

It can be confirmed that the sizes of the micelles formed by DTMs are distributed in a wide range.

The micelle, liposome, emulsion or nanoparticle may contain a membrane protein. That is, the micelle, liposome, emulsion or nanoparticle may envelop a previously-extracted membrane protein present in the cell membrane. Therefore, the micelle can be used to extract, solubilize, stabilize, crystallize or analyze a membrane protein.

The composition may further include a buffer that can help in extracting, solubilizing, stabilizing or analyzing a membrane protein.

In addition, still another aspect of the present invention provides a method of preparing a compound represented by Formula 1 below, which includes Steps 1) to 5) below:

1) synthesizing a dialkylated mono-ol derivative by introducing an alkyl group to dimethylmalonate and performing reduction;

2) synthesizing tetra-alkylated methallyl diether to which four alkyl groups are introduced by adding methallyl dichloride to the product of Step 1);

3) synthesizing a tetra-alkylated tri-ol derivative by reacting 4-(bromomethyl)-methyl-2,6,7-trioxabicyclo[2,2,2]-octane with the product of Step 2);

4) introducing a protecting group-attached saccharide by performing maltosylation on the product of Step 3); and 5) performing deprotection on the product of Step 4):

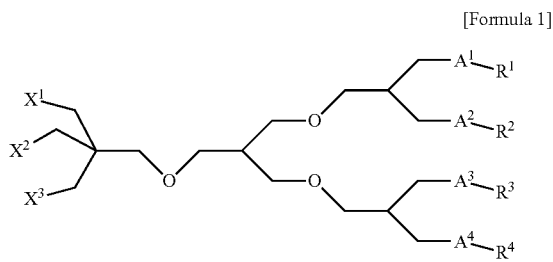

[Formula 1]

In Formula 1,

R$^1$ to R$^4$ may be each independently a substituted or unsubstituted C$_1$-C$_{15}$ alkyl group, a substituted or unsubstituted C$_1$-C$_{15}$ cycloalkyl group, or a substituted or unsubstituted C$_1$-C$_{15}$ aryl group;

A$^1$ to A$^4$ may be each independently —CH$_2$—; and

X$^1$ to X$^3$ may be each independently an oxygen-linked saccharide.

The compounds prepared according to the method may be compounds represented by Formulas 2 to 5.

In addition, yet another aspect of the present invention provides a method of preparing a compound represented by Formula 1 below, which includes Steps 1) to 5) below:

1) synthesizing a dialkylated mono-ol derivative (ether-functionalized dialkylated mono-ol derivative) by reacting an aliphatic alcohol or alkylthiol with methallyl dichloride;

2) synthesizing a tetra-alkylated mono-ol derivative (ether-functionalized tetra-alkylated mono-ol derivative) by reacting methallyl dichloride with the product of Step 1);

3) synthesizing a tetra-alkylated tri-ol derivative by reacting 4-(bromomethyl)-methyl-2,6,7-trioxabicyclo[2,2,2]-octane with the product of Step 2);

4) introducing a protecting group-attached saccharide by performing maltosylation on the product of Step 3); and 5) performing deprotection on the product of Step 4):

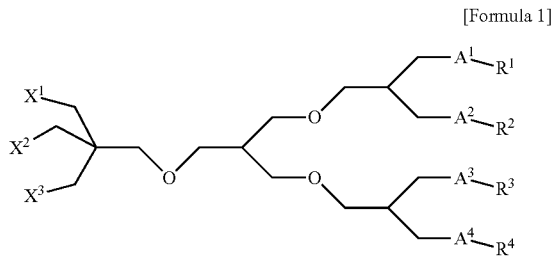

[Formula 1]

In Formula 1,

R$^1$ to R$^4$ may be each independently a substituted or unsubstituted C$_1$-C$_{15}$ alkyl group, a substituted or unsubstituted C$_1$-C$_{15}$ cycloalkyl group, or a substituted or unsubstituted C$_1$-C$_{15}$ aryl group;

A$^1$ to A$^4$ may be each independently oxygen (O) or sulfur (S); and

X$^1$ to X$^3$ may be each independently an oxygen-linked saccharide.

The compounds prepared according to the method may be compounds represented by Formulas 6 to 8.

In addition, yet another aspect of the present invention provides a method of extracting, solubilizing, stabilizing, crystallizing or analyzing a membrane protein, and particularly, a method of extracting, solubilizing, stabilizing, crystallizing or analyzing a membrane protein, which includes treating a membrane protein with a compound represented by Formula 1 below in an aqueous solution:

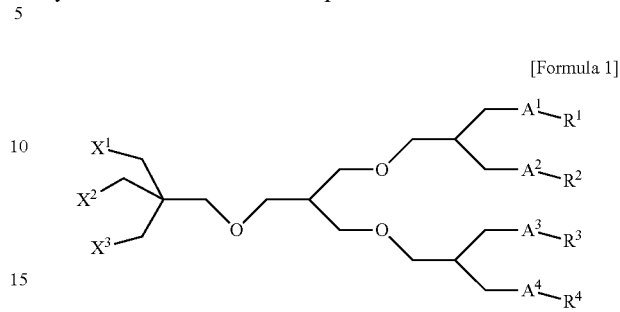

[Formula 1]

In Formula 1,

R$^1$ to R$^4$ may be each independently a substituted or unsubstituted C$_1$-C$_{15}$ alkyl group, a substituted or unsubstituted C$_1$-C$_{15}$ cycloalkyl group, or a substituted or unsubstituted C$_1$-C$_{15}$ aryl group;

A$^1$ to A$^4$ may be each independently —CH$_2$—, oxygen (O) or sulfur (S); and X$^1$ to X$^3$ may be each independently an oxygen-linked saccharide.

Preferably, R$^1$ to R$^4$ may be substituted or unsubstituted C$_1$-C$_{10}$ alkyl groups; R$^1$ to R$^4$ may be identical; A$^1$ to A$^4$ may be oxygen (O) or sulfur (S); and X$^1$ to X$^3$ may be oxygen-linked glucose or maltose.

In addition, R$^1$ to R$^4$ may be substituted or unsubstituted C$_1$-C$_{10}$ alkyl groups; R$^1$ to R$^4$ may be identical; A$^1$ to A$^4$ may be —CH$_2$—; and X$^1$ to X$^3$ may be oxygen-linked glucose or maltose.

The compounds may be 7 types of compounds represented by Formulas 2 to 8 according to an embodiment of the present invention, but the present invention is not limited thereto.

The term "membrane protein" is the collective term for proteins or glycoproteins that penetrate or are associated with the cell membrane lipid bilayer. These proteins may be present in various states, for example, may pass through the entire layers of the cell membrane, may be located on the surface layer, or may be transiently associated with the cell membrane. Examples of the membrane proteins may include, but are not limited to, receptors for enzymes, peptide hormones, local hormones, etc., hydrophilic carriers for sugars, ion channels, cell membrane antigens, etc.

The membrane protein includes any protein or glycoprotein that penetrates or is associated with the cell membrane lipid bilayer, and preferably, a complex of light harvesting-I and a reaction center (LHI-RC complex), a uric acid-xanthine/H$^+$ symporter (UapA), melibiose permease (MelB), a leucine transporter (LeuT), a G-protein coupled receptor (GPCR) or a combination of two or more thereof, but the present invention is not limited thereto.

The term "extraction of a membrane protein" refers to isolation of a membrane protein from the cell membrane.

The term "solubilization of a membrane protein" refers to dissolving a membrane protein which is not soluble in water in a micelle in an aqueous solution.

The term "stabilization of a membrane protein" refers to stable conservation of a tertiary or quaternary structure to prevent the structure and function of a membrane protein from being changed.

The term "crystallization of a membrane protein" refers to formation of a membrane protein crystal in a solution.

The term "analysis of a membrane protein" refers to analysis of the structure or function of a membrane protein. In the embodiment, the analysis of a membrane protein may be performed by a known method, and the structure of a membrane protein may be analyzed by electron microscopy, but the present invention is not limited thereto.

Advantageous Effects

When an amphiphilic compound containing a dendronic hydrophobic group according to an embodiment of the present invention is used, compared with a conventional compound, a membrane protein can be more stably stored in an aqueous solution for a longer time, and the compound of the present invention can be used in the functional and structural analyses of the membrane protein.

The functional and structural analyses of a membrane protein are one of the most popular fields in biology and chemistry, and since more than half of the novel drugs currently being developed target membrane proteins, the compound of the present invention can be applied in research of a protein structure closely associated with drug development.

BRIEF DESCRIPTION OF THE SEVERAL VIEWS OF THE DRAWINGS

FIG. 1 shows the synthetic scheme for DTM-As of the present invention.

FIG. 2 shows the synthesis scheme for DTM-Es of the present invention.

FIG. 3 shows the chemical structures of DTMs of the present invention.

FIG. 4 is a set of graphs showing dynamic light scattering (DLS) profiles of micelles formed by (a) DTM-As and (b) DTM-Es.

FIG. 5 is a set of graphs showing absorbances monitored at 875 nm and regular intervals to assess the structural stability of an LHI-RC complex dissolved in DTMs used at concentrations of (a) CMC+0.04 wt % and (b) CMC+0.2 wt %.

FIG. 6 is a set of graphs showing the results obtained by scintillation proximity assay (SPA) to assess the long-term stability of a LeuT protein solubilized in (a) DTM-As and (b) DTM-Es at a concentration of CMC+0.04 wt %.

FIG. 7 is a set of graphs showing the results obtained by SPA to assess the long-term stability of a LeuT protein solubilized in (a) DTM-As and (b) DTM-Es at a concentration of CMC+0.2 wt %.

FIG. 8 shows the result of measuring the amounts of MelB$_{st}$ protein dissolved in an aqueous solution, following the extraction of MelB$_{st}$ protein at four different temperatures (0, 45, 55 and 65° C.) using 1.5 wt % DTMs or DDM and the incubation at the same temperatures for 90 minutes:

(a) SDS-PAGE and Western Blotting results assessing the amount of MelB$_{st}$ protein extracted using each amphiphilic compound;

(b) a histogram of the amounts of MelB$_{st}$ protein extracted using each amphiphilic compound, expressed as percentages (%) of the total amount of the protein present in a membrane sample (Memb) not treated with an amphiphilic compound; and (c) a result of galactoside-binding assay.

FIG. 9 is a set of graphs showing (a) the long-term stability of $\beta_2$AR solubilized in DDM and DTMs and (b) the long-term SEC profiles of a $\beta_2$AR-G$_s$ complex in DTM-A6.

FIG. 10 shows the stability of $\beta_2$AR solubilized in DDM and DTMs, which was assessed by measuring protein activity using [$^3$H]-dihydroalprenolol (DHA), following incubation of $\beta_2$AR solubilized in CMC+0.2 wt % DDM and DTMs at room temperature for 30 minutes.

FIG. 11 shows the EM analysis results for a $\beta_2$AR-G$_s$ complex solubilized in DTM-A6.

DESCRIPTION OF THE SPECIFIC EMBODIMENTS OF THE INVENTION

Hereinafter, the present invention will be described in detail with reference to the following examples. However, the following examples are merely provided to exemplify the contents of the present invention, and do not limit the scope of the present invention. It will be interpreted that what can be easily inferred from the detailed description and examples of the present invention by those of ordinary skill in the art is within the scope of the present invention.

<Example 1> Method of Synthesizing DTM-As

The synthetic scheme for DTM-As is shown in FIG. 1. Four types of DTM-A compounds are synthesized according to a synthetic method including the following steps <1-1> to <1-7>, and the chemical structures thereof are shown in FIG. 3.

<1-1> General Procedure for Synthesis of Dialkylated Dimethylmalonate (Compound A in FIG. 1)

Dimethylmalonate (1.0 equiv.) was added dropwise to a solution of NaH (3.0 equiv.) mixed with DMSO under a N$_2$ atmosphere. Alkyl iodide (2.5 equiv.) was added in portions after the gas extraction was stopped. The resulting mixture was stirred at room temperature until the reaction was completed. The reaction was quenched by adding a cold 10% NH$_4$Cl solution, followed by washing with ethyl acetate twice. Combined ethyl acetate fractions were washed with brine, and dried over anhydrous Na$_2$SO$_4$. An organic solvent was rotary-evaporated, thereby obtaining an oily residue, which was subjected to column chromatographic purification (EtOAc/hexane), obtaining desired Compound A as colorless oil.

<1-2> Procedure for Krapcho's Decarboxylation of Compound A and Reduction of Dialkylated Monoesters (Step a in FIG. 1)

LiCl (2.2 equiv.) and H$_2$O (1.1 equiv.) were added to the solution of Compound A (1.0 equiv.) mixed with DMSO. The resulting mixture was heated to reflux for 12 hours, and diluted with water. The diluted reaction mixture was washed with ethyl acetate twice. Combined organic fractions were washed with brine, and dried over anhydrous Na$_2$SO$_4$. An oily residue obtained after the removal of an organic solvent was reduced without purification. LiAlH$_4$ (2.2 equiv.) was added to a cold solution of dialkylated monomethylester mixed with THF. The resulting gray slurry was stirred for 6 hours at room temperature under a N$_2$ atmosphere. The reaction was quenched by sequentially adding MeOH, water and a 1M HCl solution at 0° C., and then extracted with diethyl ether twice. Combined ether fractions were washed with brine, and dried over anhydrous $Na_2SO_4$. An oil residue obtained by removing the organic solvent was subjected to column chromatographic purification (EtOAc/hexane), obtaining desired Compound B as colorless oil.

<1-3> General Procedure for Synthesis of Tetra-Alkylated Methallyl Diether (Step b in FIG. 1)

NaH (3.0 equiv.) was added to a solution of Compound B well stirred in DMF (2.5 equiv.). The mixture was heated for 30 minutes at 50° C. under an inert atmosphere, and then methallyl dichloride (1.0 equiv.) was added dropwise at room temperature. The resulting mixture was stirred for 24 hours at 70° C. The reaction was quenched by the addition of methanol and dilution with ethyl acetate. Organic fractions were washed with water and brine, and dried over anhydrous $Na_2SO_4$. An oily residue obtained after the removal of a solvent under reduced pressure was purified by column chromatography (EtOAc/hexane), obtaining desired Compound C.

<1-4> General Procedure for Hydroboration (Step c in FIG. 1)

A solution of Compound C (1.0 equiv.) and $BH_3$-THF (1M, 1.1 equiv.) mixed with THF was stirred for 2 hours under a $N_2$ atmosphere at 0° C. The reaction was quenched with a 3M NaOH solution (2.2 equiv.), followed by the addition of 30 wt % $H_2O_2$. The reaction mixture was stirred again for 2 hours at room temperature, and diluted with diethyl ether. The diluted reaction mixture was washed with water and brine, and dried over anhydrous $Na_2SO_4$. An oily residue obtained after the removal of a solvent under reduced pressure was purified by column chromatography, obtaining desired Compound D.

<1-5> General Procedure for Synthesis of Tetra-Alkylated Tri-Ol (Step d in FIG. 1)

NaH (3.0 equiv.) was added to a solution of Compound D (1.0 equiv.) mixed with DMF. The resulting mixture was heated at 50° C. for 30 minutes. The mixture was cooled to room temperature, and 4-(bromomethyl)-methyl-2,6,7-trioxabicyclo[2,2,2]-octane (3.0 equiv.) dissolved in THF was added dropwise. The resulting mixture was heated for 24 hours at 100° C. After the reaction was quenched with methanol, an organic solvent was removed under reduced pressure. The resulting solid residue was dissolved in diethyl ether, washed with brine, and dried over anhydrous $Na_2SO_4$. An oily residue produced by the concentration of the organic solvent was dissolved in a DCM/MeOH mixture. Several drops of concentrated HCl were added dropwise to the resulting solution, and the resulting mixture was heated for 4 hours at 50° C. After neutralization with NaOH and the concentration of the reaction mixture, the residue was purified by column chromatography (EtOAc/hexane), obtaining desired Compound E.

<1-6> General Procedure for Maltosylation (Step e of FIG. 1)

Under a $N_2$ atmosphere, a mixture of Compound E (1.0 equiv.), AgOTf (3.6 equiv.) and 2,4,6-collidine (1.0 equiv.) mixed with anhydrous $CH_2Cl_2$ was stirred at −45° C. A solution of perbenzoylated maltosylbromide (3.6 equiv.) mixed with $CH_2Cl_2$ was added dropwise to the resulting suspension. After stirring for 30 minutes at −45° C., the reaction mixture was heated to 0° C. and stirred for 30 minutes. After the completion of the reaction (indicated by TLC), pyridine was added to the reaction mixture, followed by dilution with $CH_2Cl_2$ and filtration over Celite. The resulting filtrate was washed sequentially with a 1M $Na_2S_2O_3$ aqueous solution, a 0.1M HCl aqueous solution and brine. An organic layer was dried with anhydrous $Na_2SO_4$, and the solvent was removed by a rotary evaporator. The residue was purified by silica gel column chromatography (EtOAc/hexane), obtaining desired Compound F as a glassy solid.

<1-7> General Procedure for Deprotection (Step f of FIG. 1)

O-benzoylated compound F was dissolved in MeOH, and treated with a required amount of a methanol solution of 0.5M NaOMe, such that the final concentration of NaOMe was 0.05M. The reaction mixture was stirred for 6 hours at room temperature, and then neutralized with Amberlite IR-120 ($H^+$ form). The resin was removed by filtration and washed with MeOH, and a solvent was removed from the combined filtrate in vacuo. 50 mL of diethyl ether was added to the residue dissolved in a 2 mL MeOH:$CH_2Cl_2$ (1:1) mixture, obtaining desired Compound G as a white solid.

<Preparation Example 1> Synthesis of DTM-A5

<1-1> Synthesis of Dimethyl 2-Pentylmalonate (Compound A1)

Compound A1 was synthesized in 90% yield according to the procedure of Example 1-1. $^1$H NMR (400 MHz, $CDCl_3$): δ 3.69 (s, 6H), 1.34-1.05 (m, 16H), 0.87 (t, J=7.2 Hz, 6H); $^{13}$CNMR (100 MHz, $CDCl_3$): δ 172.7, 57.8, 52.4, 32.5, 32.2, 23.9, 22.6, 14.2.

<1-2> Synthesis of 2-pentylheptan-1-ol (Compound B5)

Compound B5 was synthesized in 89% yield according to the procedure of Example 1-2. $^1$H NMR (400 MHz, $CDCl_3$): δ 3.53 (d, J=5.6 Hz, 2H), 1.48-1.40 (m, 1H), 1.36-1.18 (m, 16H), 0.87 (t, J=6.4 Hz, 6H); $^{13}$CNMR (100 MHz, $CDCl_3$): δ 65.8, 40.7, 32.5, 31.1, 26.7, 22.9, 14.3.

<1-3> Synthesis of 6-(((2-(((2-pentylheptyl)oxy) methyl)allyl)oxy)methyl)undecane (Compound C9)

Compound C9 was synthesized in 72% yield according to the procedure of Example 1-3. $^1$H NMR (400 MHz, $CDCl_3$): δ 5.14 (s, 2H), 3.94 (s, 4H), 3.28 (d, J=6.0 Hz, 4H), 1.60-1.53 (m, 2H), 1.32-1.18 (m, 32H), 0.88 (t, J=8.0 Hz, 12H); $^{13}$CNMR (100 MHz, $CDCl_3$): δ 143.5, 113.0, 73.7, 71.7, 38.3, 31.9, 29.8, 26.8, 22.7, 14.1.

<1-4> Synthesis of 3-((2-pentylheptyl)oxy)-2-(((2-pentylheptyl)oxy)methyl)propan-1-ol (Compound D13)

Compound D13 was synthesized in 88% yield according to the procedure of Example 1-4. $^1$H NMR (400 MHz, $CDCl_3$): δ 3.76 (t, J=4.0 Hz, 2H), 3.53-3.48 (m, 4H), 3.29 (d, J=8.0 Hz, 4H), 2.12-2.05 (m, 1H), 1.56-1.50 (m, 2H), 1.32-1.18 (m, 32H), 0.88 (t, J=4.8 Hz, 12H); $^{13}$CNMR (100 MHz, CDCl$_3$): δ 74.9, 71.6, 65.4, 41.4, 38.4, 32.1, 30.0, 27.0, 22.9, 14.3.

<1-5> Synthesis of 2-(hydroxymethyl)-2-((3-((2-pentylheptyl)oxy)-2-(((2-pentylheptyl)oxy)methyl) propoxy)methyl)propane-1,3-diol (Compound E17)

Compound E17 was synthesized in 42% yield according to the procedure of Example 1-5. $^1$H NMR (400 MHz, CDCl$_3$): δ 3.62 (s, 6H), 3.41 (d, J=4.0 Hz, 2H), 3.38 (s, 2H), 3.32 (d, J=4.0 Hz, 4H) 3.18 (d, J=4.0 Hz, 4H), 2.97 (br s, 3H), 2.10-2.07 (m, 1H), 1.50-1.41 (m, 2H), 1.36-1.18 (m, 32H), 0.88 (t, J=6.4 Hz, 12H); $^{13}$CNMR (100 MHz, CDCl$_3$): δ 74.8, 73.6, 71.0, 69.7, 64.9, 45.2, 40.2, 38.3, 32.5, 31.6, 26.7, 22.9, 14.3.

<1-6> Synthesis of DTM-A5a

DTM-A5a was synthesized in 65% yield according to the general maltosylation procedure of Example 1-6. $^1$H NMR (400 MHz, CDCl$_3$): δ 8.06 (d, J=8.0 Hz, 6H), 7.96 (d, J=8.0 Hz, 6H), 7.87-7.84 (m, 18H), 7.78 (d, J=8.0 Hz, 6H), 7.66 (d, J=8.0 Hz, 6H), 7.55-7.45 (m, 18H), 7.43-7.31 (m, 36H), 7.27-7.21 (m, 9H), 6.08 (t, J=8.0 Hz, 3H), 5.65 (d, J=8.0 Hz, 3H), 5.62 (d, J=8.0 Hz, 3H), 5.44 (t, J=8.0 Hz, 3H), 5.18-5.08 (m, 6H), 4.55 (q, J=12.0 Hz, 6H), 4.30-4.22 (m, 9H), 4.16-4.10 (m, 3H), 3.68 (t, J=10.0 Hz, 6H), 3.17-3.04 (m, 15H), 2.97 (d, J=12.0 Hz, 3H), 1.96-1.87 (m, 1H), 1.48-42 (m, 2H), 1.28-1.08 (m, 32H), 0.85 (t, J=7.0 Hz, 12H); $^{13}$CNMR (100 MHz, CDCl$_3$): δ 166.0, 165.7, 165.4, 164.9, 164.7, 133.4, 133.1, 129.8, 129.6, 129.5, 129.4, 129.3, 128.8, 128.7, 128.6, 128.3, 128.2, 100.9, 95.8, 74.7, 74.3, 72.3, 71.2, 70.2, 69.8, 69.1, 68.8, 67.7, 63.4, 62.4, 60.3, 53.5, 44.8, 40.1, 38.2, 31.9, 31.4, 29.8, 26.8, 22.7, 20.9, 14.2.

<1-7> Synthesis of DTM-A5

DTM-A5 was synthesized in 92% yield according to the general deprotection procedure of Example 1-7. $^1$H NMR (400 MHz, CD$_3$OD): δ 5.14 (d, J=4.0 Hz, 3H), 4.34 (d, J=8.0 Hz, 3H), 3.97 (d, J=8.0 Hz, 3H), 3.87 (m, 3H), 3.83-3.79 (m, 6H), 3.68-3.58 (m, 15H), 3.52 (t, J=10.0 Hz, 3H), 3.47-3.42 (m, 9H), 3.31-3.30 (m, 3H), 3.30-3.28 (m, 3H), 3.27-3.21 (m, 9H), 2.15-2.07 (m, 1H), 1.61-1.52 (m, 2H), 1.39-1.21 (m, 32H), 0.91 (t, J=7.0 Hz, 12H); $^{13}$CNMR (100 MHz, CD$_3$OD): 105.0, 102.9, 81.3, 77.8, 76.5, 75.5, 75.1, 74.8, 74.2, 71.5, 70.4, 70.1, 62.7, 62.3, 48.5, 46.6, 41.6, 39.5, 33.6, 32.7, 27.7, 23.8, 14.7. HRMS (FAB$^+$): calcd. for C$_{69}$H$_{128}$O$_{36}$ [M+Na]$^+$ 1555.8083, found 1555.8087.

<Preparation Example 2> Synthesis of DTM-A6

<2-1> Synthesis of Dimethyl 2-Hexylmalonate (Compound A2)

Compound A2 was synthesized in 92% yield according to the procedure of Example 1-1. $^1$H NMR (400 MHz, CDCl$_3$): δ 3.70 (s, 6H), 1.88-1.84 (m, 4H), 1.35-1.10 (m, 12H), 1.09-1.05 (m, 4H), 0.87 (t, J=6.8 Hz, 6H); $^{13}$CNMR (100 MHz, CDCl$_3$): δ 172.6, 57.8, 52.4, 32.5, 31.7, 29.6, 24.1, 22.7, 14.2.

<2-2> 2-Synthesis of Hexyloctan-1-Ol (Compound B6)

Compound B6 was synthesized in 87% yield according to the procedure of Example 1-2. $^1$H NMR (400 MHz, CDCl$_3$): δ 3.53 (d, J=5.2 Hz, 2H), 1.47-1.43 (m, 1H), 1.38-1.18 (m, 20H), 0.88 (t, J=6.4 Hz, 6H); $^{13}$CNMR (100 MHz, CDCl$_3$): δ 65.2, 40.5, 32.0, 30.6, 26.9, 25.9, 22.7, 14.3.

<2-3> Synthesis of 7-(((2-(((2-hexyloctyl)oxy) methyl)allyl)oxy)methyl)tridecane (Compound C10)

Compound C10 was synthesized in 72% yield according to the procedure of Example 1-3. $^1$H NMR (400 MHz, CDCl$_3$): δ 5.15 (s, 2H), 3.94 (s, 4H), 3.28 (d, J=6.0 Hz, 2H), 1.60-1.53 (m, 2H), 1.32-1.18 (m, 40H), 0.88 (t, J=8.0 Hz, 12H); $^{13}$CNMR (100 MHz, CDCl$_3$): δ 143.5, 113.0, 73.7, 71.7, 38.3, 31.9, 31.5, 29.8, 26.8, 22.7, 14.1.

<2-4> Synthesis of 3-((2-hexyloctyl)oxy)-2-(((2-hexyloctyl)oxy)methyl)propan-1-ol (Compound D14)

Compound D14 was synthesized in 86% yield according to the procedure of Example 1-4. $^1$H NMR (400 MHz, CDCl$_3$): δ 3.76 (t, J=5.2 Hz, 2H), 3.55-3.46 (m, 4H), 3.28 (d, J=6.0 Hz, 4H), 2.93 (t, J=5.6 Hz, 1H), 2.14-2.07 (m, 1H), 1.58-1.50 (m, 2H), 1.32-1.18 (m, 40H), 0.88 (t, J=6.8 Hz, 12H); $^{13}$CNMR (100 MHz, CDCl$_3$): δ 74.9, 71.6, 65.3, 41.4, 38.5, 32.1, 31.6, 29.9, 27.0, 22.9, 14.3.

<2-5> Synthesis of 2-((3-((2-hexyloctyl)oxy)-2-(((2-hexyloctyl)oxy)methyl) propoxy)methyl)-2-(hydroxymethyl)propane-1,3-diol (Compound E18)

Compound E18 was synthesized in 44% yield according to the procedure of Example 1-5. $^1$H NMR (400 MHz, CDCl$_3$): δ 3.66 (s, 6H), 3.51 (br s, 3H), 3.46 (d, J=6.0 Hz, 2H), 3.39 (d, J=6.0 Hz, 4H), 3.25 (d, J=4.2 Hz, 4H), 2.17-2.11 (m, 1H), 1.54-1.41 (m, 2H), 1.36-1.18 (m, 40H), 0.88 (t, J=6.4 Hz, 12H); $^{13}$CNMR (100 MHz, CDCl$_3$): δ 74.8, 73.4, 70.8, 69.6, 64.2, 45.2, 40.2, 38.2, 32.0, 31.6, 29.9, 26.9, 22.8, 14.3.

<2-6> Synthesis of DTM-A6a

DTM-A6a was synthesized in 63% yield according to the general maltosylation procedure of Example 1-6. $^1$H NMR (400 MHz, CDCl$_3$): δ 8.13 (d, J=8.0 Hz, 6H), 8.05 (d, J=8.0 Hz, 6H), 7.94-7.87 (m, 18H), 7.81 (d, J=8.0 Hz, 6H), 7.70 (d, J=8.0 Hz, 6H), 7.56-7.53 (m, 6H), 7.48-7.40 (m, 18H), 7.38-7.33 (m, 12H), 7.31-7.27 (m, 15H), 7.24 (t, J=8.0 Hz, 6H), 7.16 (t, J=8.0 Hz, 6H), 6.18 (t, J=8.0 Hz, 3H), 5.73 (t, J=12.0 Hz, 6H), 5.51 (t, J=8.0 Hz, 3H), 5.26-5.20 (m, 6H), 4.64 (q, J=12.0 Hz, 6H), 4.42-4.34 (m, 9H), 4.24 (d, J=12.0 Hz, 3H), 3.80 (d, J=8.0 Hz, 3H), 3.75 (d, J=4.0 Hz, 3H), 3.31-3.06 (m, 18H), 2.05-1.97 (m, 1H), 1.56-1.48 (m, 2H), 1.34-1.20 (m, 40H), 0.88 (t, J=6.0 Hz, 12H); $^{13}$CNMR (100 MHz, CDCl$_3$): δ 166.0, 165.7, 165.4, 164.9, 164.7, 133.4, 133.1, 129.8, 129.6, 129.5, 129.4, 129.3, 128.8, 128.7, 128.6, 128.3, 128.2, 100.9, 95.8, 74.7, 74.3, 72.3, 71.2, 70.2, 69.8, 69.1, 68.9, 68.8, 67.7, 63.4, 62.4, 60.3, 53.5, 44.8, 40.1, 38.2, 31.9, 31.4, 31.3, 29.8, 26.8, 22.7, 20.9, 14.2.

<2-7> Synthesis of DTM-A6

DTM-A6 was synthesized in 90% yield according to the general deprotection procedure of Example 1-7. $^1$H NMR (400 MHz, CD$_3$OD): δ 5.13 (d, J=4.0 Hz, 3H), 4.34 (d, J=8.0 Hz, 3H), 3.96 (d, J=10.0 Hz, 3H), 3.84 (m, 3H), 3.81-3.79 (m, 7H), 3.67-3.60 (m, 15H), 3.54 (t, J=11.6 Hz, 3H), 3.45-3.42 (m, 9H), 3.38-3.30 (m, 3H), 3.26-3.22 (m, 10H), 2.14-2.09 (m, 1H), 1.60-1.50 (m, 2H), 1.37-1.22 (m, 40H), 0.90 (t, J=6.8 Hz, 12H); $^{13}$CNMR (100 MHz, CD$_3$OD): δ 105.1, 102.9, 81.4, 77.8, 76.6, 75.6, 75.1, 74.8, 74.2, 71.5, 70.4, 70.1, 62.8, 62.3, 48.5, 46.6, 41.7, 39.5, 33.2, 32.8, 32.7, 31.0, 28.0, 23.9, 14.7. HRMS (FAB$^+$): calcd. for C$_{73}$H$_{136}$O$_{36}$ [M+Na]$^+$ 1611.8709, found 1611.8707.

<Preparation Example 3> Synthesis of DTM-A7

<3-1> Synthesis of Dimethyl 2-Heptylmalonate (Compound A3)

Compound A3 was synthesized in 92% yield according to the procedure of Example 1-1. $^1$H NMR (400 MHz, CDCl$_3$): δ 3.69 (s, 6H), 1.34-1.15 (m, 24H), 0.88 (t, J=6.8 Hz, 6H); $^{13}$CNMR (100 MHz, CDCl$_3$): δ 172.7, 57.8, 52.4, 32.5, 32.0, 30.0, 29.2, 24.2, 22.9, 14.3.

<3-2> Synthesis of 2-heptylnonan-1-ol (Compound B7)

Compound B7 was synthesized in 85% yield according to the procedure of Example 1-2. $^1$H NMR (400 MHz, CDCl$_3$): δ 3.53 (d, J=4.0 Hz, 2H), 1.47-1.43 (m, 1H), 1.35-1.19 (m, 24H), 0.87 (t, J=7.2 Hz, 6H); $^{13}$CNMR (100 MHz, CDCl$_3$): δ 65.9, 40.7, 32.1, 31.1, 30.2, 29.5, 27.1, 22.9, 14.3.

<3-3> Synthesis of 8-(((2-(((2-heptylnonyl)oxy) methyl)allyl)oxy)methyl) pentadecane (Compound C11)

Compound C11 was synthesized in 74% yield according to the procedure of Example 1-3. $^1$H NMR (400 MHz, CDCl$_3$): δ 5.15 (s, 2H), 3.94 (s, 4H), 3.28 (d, J=6.0 Hz, 4H), 1.60-1.53 (m, 2H), 1.36-1.18 (m, 48H), 0.88 (t, J=6.8 Hz, 12H); $^{13}$CNMR (100 MHz, CDCl$_3$): δ 143.7, 113.2, 74.0, 71.9, 38.5, 32.1, 31.7, 30.3, 29.6, 27.1, 22.9, 14.3.

<3-4> Synthesis of 3-((2-heptylnonyl)oxy)-2-(((2-heptylnonyl)oxy)methyl)propan-1-ol (Compound D15)

Compound D15 was synthesized in 86% yield according to the procedure of Example 1-4. $^1$H NMR (400 MHz, CDCl$_3$): δ 3.76 (t, J=5.2 Hz, 2H), 3.55-3.46 (m, 4H), 3.28 (d, J=6.0 Hz, 4H), 2.92 (t, J=5.6 Hz, 1H), 2.12-2.07 (m, 1H), 1.58-1.50 (m, 2H), 1.32-1.18 (m, 48H), 0.88 (t, J=6.8 Hz, 12H); $^{13}$CNMR (100 MHz, CDCl$_3$): δ 75.0, 71.8, 63.3, 41.4, 38.5, 32.1, 30.2, 29.9, 29.5, 27.0, 22.8, 14.2.

<3-5> Synthesis of 2-((3-((2-heptylnonyl)oxy)-2-(((2-heptylnonyl)oxy)methyl) propoxy)methyl)-2-(hydroxymethyl)propane-1,3-diol (Compound E19)

Compound E19 was synthesized in 44% yield according to the procedure of Example 1-5. $^1$H NMR (400 MHz, CDCl$_3$): δ 3.69 (s, 6H), 3.48 (d, J=6.0 Hz, 2H), 3.44 (s, 2H), 3.39 (d, J=4.0 Hz, 4H), 3.25 (d, J=8.0 Hz, 4H), 3.03 (br s, 3H), 2.17-2.14 (m, 1H), 1.58-1.51 (m, 2H), 1.36-1.18 (m, 48H), 0.88 (t, J=6.4 Hz, 12H); $^{13}$CNMR (100 MHz, CDCl$_3$): δ 74.9, 73.6, 70.9, 69.7, 65.0, 45.2, 40.2, 38.3, 32.1, 31.6, 30.3, 29.6, 27.0, 22.9, 14.3.

<3-6> Synthesis of DTM-A7a

DTM-A7a was synthesized in 66% yield according to the general maltosylation procedure of Example 1-6. $^1$H NMR (400 MHz, CDCl$_3$): δ 8.06 (d, J=8.0 Hz, 6H), 7.96 (d, J=8.0 Hz, 6H), 7.87-7.84 (m, 18H), 7.78 (d, J=8.0 Hz, 6H), 7.66 (d, J=8.0 Hz, 6H), 7.53-7.44 (m, 18H), 7.43-7.31 (m, 36H), 7.27-7.21 (m, 9H), 6.09 (t, J=8.0 Hz, 3H), 5.65 (d, J=8.0 Hz, 3H), 5.62 (d, J=8.0 Hz, 3H), 5.42 (t, J=8.0 Hz, 3H), 5.18-5.09 (m, 6H), 4.55 (q, J=12.0 Hz, 6H), 4.34-4.23 (m, 9H), 4.17-4.11 (m, 3H), 3.68 (d, J=8.0 Hz, 3H), 3.66 (d, J=8.0 Hz, 3H) 3.25-3.06 (m, 15H), 2.97 (d, J=12.0 Hz, 3H), 1.95-1.85 (m, 1H), 1.46-1.41 (m, 2H), 1.28-1.12 (m, 48H), 0.86 (t, J=8.0 Hz, 12H); $^{13}$CNMR (100 MHz, CDCl$_3$): δ 166.1, 165.8, 165.7, 165.5, 165.0, 164.7, 133.4, 133.2, 129.9, 129.8, 129.7, 129.5, 129.4, 128.9, 128.7, 128.6, 128.4, 128.2, 100.9, 95.9, 74.8, 74.4, 72.4, 72.3, 72.2, 71.2, 70.3, 69.9, 69.0, 65.8, 63.5, 62.4, 60.3, 53.5, 44.8, 40.2, 38.2, 31.9, 31.4, 29.4, 26.9, 22.7, 15.3, 14.2.

<3-7> Synthesis of DTM-A7

DTM-A6 was synthesized in 90% yield according to the general deprotection procedure of Example 1-7. $^1$H NMR (400 MHz, CD$_3$OD): δ 5.14 (d, J=4.0 Hz, 3H), 4.34 (d, J=8.0 Hz, 3H), 3.97 (d, J=8.0 Hz, 3H), 3.87 (m, 3H), 3.81-3.79 (m, 6H), 3.67-3.59 (m, 15H), 3.52 (t, J=10.0 Hz, 3H), 3.45-3.42 (m, 9H), 3.38-3.30 (m, 6H), 3.27-3.21 (m, 9H), 2.13-2.08 (m, 1H), 1.59-1.51 (m, 2H), 1.37-1.25 (m, 48H), 0.90 (t, J=6.4 Hz, 12H); $^{13}$CNMR (100 MHz, CD$_3$OD): δ 105.0, 102.9, 81.4, 77.8, 76.6, 75.6, 75.1, 74.8, 74.2, 71.5, 70.9, 70.4, 66.9, 62.7, 62.3, 46.6, 41.7, 39.5, 33.2, 32.7, 30.6, 28.1, 23.9, 15.6, 14.7. HRMS (FAB$^+$): calcd. for C$_{77}$H$_{144}$O$_{36}$ [M+Na]$^+$1667.9335, found 1667.9330.

<Preparation Example 4> Synthesis of DTM-A8

<4-1> Synthesis of dimethyl 2-octylmalonate (Compound A4)

Compound A4 was synthesized in 93% yield according to the procedure of Example 1-1. $^1$H NMR (400 MHz, CDCl$_3$): δ 3.70 (s, 6H), 1.88-1.84 (m, 4H), 1.34-1.15 (m, 20H), 1.12-1.03 (m, 4H), 0.87 (t, J=6.4 Hz, 6H); $^{13}$CNMR (100 MHz, CDCl$_3$): δ 172.6, 57.8, 52.4, 32.5, 32.0, 30.0, 29.4, 29.3, 24.1, 22.8, 14.2.

<4-2> Synthesis of 2-octyldecan-1-ol (Compound B8)

Compound B8 was synthesized in 87% yield according to the procedure of Example 1-2. $^1$H NMR (400 MHz, CDCl$_3$): δ 3.53 (d, J=4.0 Hz, 2H), 1.47-1.43 (m, 1H), 1.32-1.18 (m, 28H), 0.88 (t, J=8.0 Hz, 6H); $^{13}$CNMR (100 MHz, CDCl$_3$): δ 65.9, 40.7, 32.1, 31.1, 30.3, 29.8, 29.5, 27.1, 22.9, 14.3.

<4-3> Synthesis of 9-(((2-(((2-octyldecyl)oxy) methyl)allyl)oxy)methyl)heptadecane (Compound C12)

Compound C12 was synthesized in 70% yield according to the procedure of Example 1-3. $^1$H NMR (400 MHz, CDCl$_3$): δ 5.15 (s, 2H), 3.94 (s, 4H), 3.28 (d, J=6.0 Hz, 4H), 1.59-1.51 (m, 2H), 1.36-1.18 (m, 56H), 0.88 (t, J=6.8 Hz, 12H); $^{13}$CNMR (100 MHz, CDCl$_3$): δ 143.7, 113.2, 74.0, 71.9, 38.5, 32.1, 31.7, 30.3, 29.8, 29.6, 27.1, 22.9, 14.3.

<4-4> Synthesis of 3-((2-octyldecyl)oxy)-2-(((2-octyldecyl)oxy)methyl)propan-1-ol (Compound D16)

Compound D16 was synthesized in 89% yield according to the procedure of Example 1-4. $^1$H NMR (400 MHz, CDCl$_3$): δ 3.76 (t, J=5.2 Hz, 2H), 3.54-3.46 (m, 4H), 3.28 (d, J=6.0 Hz, 4H), 2.96 (t, J=5.6 Hz, 1H), 2.13-2.07 (m, 1H), 1.58-1.50 (m, 2H), 1.32-1.18 (m, 56H), 0.88 (t, J=6.8 Hz, 12H); $^{13}$CNMR (100 MHz, CDCl$_3$): δ 75.0, 71.8, 63.3, 41.4, 38.5, 32.1, 31.7, 30.2, 29.9, 29.5, 27.0, 22.8, 14.2.

<4-5> Synthesis of 2-(hydroxymethyl)-2-((3-((2-octyldecyl)oxy)-2-(((2-octyldecyl)oxy)methyl)propoxy)methyl)propane-1,3-diol (Compound E20)

Compound E20 was synthesized in 44% yield according to the procedure of Example 1-5. $^1$H NMR (400 MHz, CDCl$_3$): δ 3.71 (s, 6H), 3.48 (s, 2H), 3.39 (d, J=4.0 Hz, 4H), 3.25 (d, J=8.0 Hz, 4H), 2.60 (br s, 3H), 2.17-2.14 (m, 1H), 1.53-1.51 (m, 2H), 1.36-1.18 (m, 56H), 0.88 (t, J=6.4 Hz, 12H); $^{13}$CNMR (100 MHz, CDCl$_3$): δ 74.7, 73.5, 70.8, 69.6, 64.5, 53.3, 45.2, 40.2, 38.2, 32.1, 31.5, 30.3, 29.8, 27.0, 22.8, 14.2.

<4-6> Synthesis of DTM-A8a

DTM-A8a was synthesized in 62% yield according to the general maltosylation procedure of Example 1-6. $^1$H NMR (400 MHz, CDCl$_3$): δ 8.09 (d, J=8.0 Hz, 6H), 7.98 (d, J=8.0 Hz, 6H), 7.89-7.84 (m, 18H), 7.79 (d, J=8.0 Hz, 6H), 7.68 (d, J=8.0 Hz, 6H), 7.57-7.46 (m, 18H), 7.43-7.37 (m, 16H), 7.36-7.29 (m, 17H), 7.26-7.18 (m, 12H), 6.13 (t, J=8.0 Hz, 3H), 5.67 (t, J=8.0 Hz, 6H), 5.46 (t, J=8.0 Hz, 3H), 5.22-5.13 (m, 6H), 4.59 (q, J=10.0 Hz, 6H), 4.37-4.28 (m, 9H), 4.19 (d, J=12.0 Hz, 3H), 3.75 (d, J=8.0 Hz, 3H), 3.70 (d, J=8.0 Hz, 3H), 3.30-3.04 (m, 15H), 3.02 (d, J=12.0 Hz, 3H), 2.01-1.90 (m, 1H), 1.49-1.41 (m, 2H), 1.28-1.12 (m, 56H), 0.87 (t, J=6.8 Hz, 12H); $^{13}$CNMR (100 MHz, CDCl$_3$): δ 166.1, 165.8, 165.5, 165.1, 164.8, 133.6, 133.4, 133.2, 129.9, 129.7, 129.6, 129.5, 129.4, 128.9, 128.8, 128.7, 128.6, 128.4, 128.2, 100.9, 95.9, 74.8, 74.4, 72.3, 72.2, 71.3, 69.9, 69.0, 67.8, 63.5, 62.4, 53.5, 44.9, 40.2, 38.3, 31.9, 31.4, 30.2, 29.7, 29.5, 26.9, 22.8, 14.2.

<4-7> Synthesis of DTM-A8

DTM-A8 was synthesized in 94% yield according to the general deprotection procedure of Example 1-7. $^1$H NMR (400 MHz, CD$_3$OD): δ 5.15 (d, J=4.0 Hz, 3H), 4.34 (d, J=8.0 Hz, 3H), 3.96 (d, J=10.0 Hz, 3H), 3.87 (m, 3H), 3.83-3.79 (m, 6H), 3.68-3.59 (m, 15H), 3.52 (t, J=12.0 Hz, 4H), 3.45-3.42 (m, 10H), 3.38-3.30 (m, 4H), 3.27-3.22 (m, 9H), 2.12-2.08 (m, 1H), 1.58-1.51 (m, 2H), 1.38-1.27 (m, 56H), 0.90 (t, J=6.8 Hz, 12H). $^{13}$CNMR (100 MHz, CD$_3$OD): δ 105.1, 103.0, 81.4, 77.9, 76.6, 75.6, 75.2, 74.8, 74.2, 71.5, 70.4, 70.1, 67.3, 62.8, 62.3, 46.7, 41.7, 39.5, 33.3, 32.7, 31.7, 30.9, 30.6, 28.1, 23.9, 15.6, 14.7. HRMS (FAB$^+$): calcd. for C$_{81}$H$_{152}$O$_{36}$ [M+Na]$^+$1723.9961, found 1723.9956.

<Example 2> Synthesis of DTM-Es

The synthetic scheme for DTM-Es is shown in FIG. 2. Three types of DTM-E compounds were synthesized according to the synthetic method including the following steps <2-1> to <2-7>, and the chemical structures of the compounds are shown in FIG. 3.

<2-1> General Procedure for Synthesizing Dialkylated Methallyl Diether (Compound A of FIG. 2)

NaH (3.0 equiv.) was added to a well-stirred solution of THF and an aliphatic alcohol (aliphatic alcohol, 2.5 equiv.) at 0° C. under a N$_2$ atmosphere. After stirring for 30 minutes, methallyl dichloride (1.0 equiv.) was added dropwise. The resulting mixture was refluxed for 24 hours, and then the reaction was quenched with methanol. The reaction mixture was diluted with ethyl acetate, washed with water and brine, and dried over anhydrous Na$_2$SO$_4$. An oily residue obtained by the removal of a solvent was purified by column chromatography (Hex/EtOAc), obtaining pure, desired Compound A.

<2-2> General Procedure of Hydroboration (Step a of FIG. 2)

Compound A (1.0 equiv.) mixed with THF and a BH$_3$-THF solution (1M, 1.1 equiv.) were stirred for 2 hours under a N$_2$ atmosphere at 0° C. The reaction was quenched with a 3M NaOH solution (2.2 equiv.), and then 30 wt % H$_2$O$_2$ was added. The reaction mixture was stirred again for 2 hours at room temperature, and diluted with diethyl ether. The diluted reaction mixture was washed with water and brine, and dried over anhydrous Na$_2$SO$_4$. An oily residue obtained by the removal of a solvent was purified by column chromatography, obtaining desired Compound B.

<2-3> General Procedure for Synthesizing Tetra-Alkylated Methallyl Diether (Step b of FIG. 2)

NaH (3.0 equiv.) was added to a Compound B solution (2.5 equiv.) well stirred with DMF. The mixture was heated for 30 minutes at 50° C. under an inert atmosphere, and methallyl dichloride (1.0 equiv.) was added dropwise at room temperature. The resulting mixture was stirred for 24 hours at 70° C. The reaction was quenched by addition of methanol and dilution with ethyl acetate. Organic fractions were washed with water and brine, and dried over anhydrous Na$_2$SO$_4$. An oily residue obtained by the removal of a solvent under reduced pressure was purified by column chromatography (EtOAc/hexane), obtaining desired Compound C.

<2-4> General Procedure for Hydroboration (Step a of FIG. 2)

Compound C (1.0 equiv.) mixed with THF and a BH$_3$-THF solution (1M, 1.1 equiv.) were stirred for 2 hours under a N$_2$ atmosphere at 0° C. The reaction was quenched with a 3M NaOH solution (2.2 equiv.), and then 30 wt % H$_2$O$_2$ was added. The reaction mixture was stirred again for 2 hours at room temperature, and diluted with diethyl ether. The diluted reaction mixture was washed with water and brine, and dried over anhydrous Na$_2$SO$_4$. An oily residue obtained by the removal of a solvent was purified by column chromatography, obtaining desired Compound D.

<2-5> General Procedure for Synthesizing Tetra-Alkylated Tri-Ol (Step c of FIG. 2)

NaH (3.0 equiv.) was added to a Compound D solution mixed with DMF (1.0 equiv.). The mixture was heated at 50° C. for 30 minutes. The mixture was cooled to room temperature, and 4-(bromomethyl)-methyl-2,6,7-trioxabicyclo[2,2,2]-octane (3.0 equiv.) dissolved in THF was added dropwise. The resulting mixture was heated for 24 hours at 100° C. The reaction was quenched with methanol, and then an organic solvent was removed under reduced pressure. The resulting solid residue was dissolved in diethyl ether, washed with brine, and dried over anhydrous $Na_2SO_4$. An oily residue produced by concentrating an organic solvent was dissolved in a DCM/MeOH mixture. Several drops of concentrated HCl were added dropwise to this solution, and the resulting mixture was heated for 4 hours at 50° C. After neutralization with NaOH and the concentration of the resulting mixture, the residue was purified by column chromatography (EtOAc/hexane), obtaining desired compound E.

<2-6> General Procedure for Maltosylation (Step d of FIG. 2)

Under a $N_2$ atmosphere, a mixture of Compound E (1.0 equiv.), AgOTf (3.6 equiv.) and 2,4,6-collidine (1.0 equiv.) mixed with anhydrous $CH_2Cl_2$ was stirred at −45° C. A solution of perbenzoylated maltosylbromide (3.6 equiv.) mixed with $CH_2Cl_2$ was added dropwise to the resulting suspension. After stirring for 30 minutes at −45° C., the reaction mixture was heated to 0° C. and stirred for 30 minutes. After the completion of the reaction (indicated by TLC), pyridine was added to the reaction mixture, followed by dilution with $CH_2Cl_2$ and filtration over Celite. The resulting filtrate was washed sequentially with a 1M $Na_2S_2O_3$ aqueous solution, a 0.1M HCl aqueous solution and brine. An organic layer was dried with anhydrous $Na_2SO_4$, and the solvent was removed by a rotary evaporator. The residue was purified by silica gel column chromatography (EtOAc/hexane), obtaining desired Compound F as a glassy solid.

<2-7> General Procedure for Deprotection (Step e of FIG. 2)

O-benzoylated compound F was dissolved in MeOH, and treated with a required amount of a methanol solution of 0.5M NaOMe, such that the final concentration of NaOMe was 0.05M. The reaction mixture was stirred for 6 hours at room temperature, and then neutralized with Amberlite IR-120 ($H^+$ form). The resin was removed by filtration and washed with MeOH, and a solvent was removed from the combined filtrate in vacuo. 50 mL of diethyl ether was added to the residue dissolved in a 2 mL MeOH:$CH_2Cl_2$ (1:1) mixture, obtaining desired Compound G as a white solid.

<Preparation Example 5> Synthesis of DTM-E5

<5-1> Synthesis of 1-((2-((pentyloxy)methyl)allyl)oxy)pentane (Compound A21)

Compound A21 was synthesized in 90% yield according to the procedure of Example 2-1. $^1$H NMR (400 MHz, $CDCl_3$): δ 5.16 (s, 2H), 3.97 (s, 4H), 3.41 (t, J=6.6 Hz, 4H), 1.62-1.55 (m, 4H), 1.35-1.31 (m, 8H), 0.88 (t, J=7.2 Hz, 6H); $^{13}$CNMR (100 MHz, $CDCl_3$): δ 143.5, 113.4, 71.6, 70.6, 29.6, 28.5, 22.7, 14.2.

<5-2> Synthesis of 3-(pentyloxy)-2-((pentyloxy)methyl)propan-1-ol (Compound B24)

Compound B24 was synthesized in 91% yield according to the procedure of Example 2-2. $^1$H NMR (400 MHz, $CDCl_3$): δ 3.75 (d, J=4.8 Hz, 2H), 3.52 (m, 4H), 3.41 (t, J=6.6 Hz, 4H), 3.04 (br s, 1H), 2.09 (m, 1H), 1.60-1.53 (m, 4H), 1.33-1.28 (m, 8H), 0.88 (t, J=6.8 Hz, 6H); $^{13}$CNMR (100 MHz, $CDCl_3$): δ 71.7, 64.6, 62.6, 41.4, 29.4, 28.4, 22.6, 14.1.

<5-3> Synthesis of 12-methylene-8,16-bis((pentyloxy)methyl)-6,10,14,18-tetraoxatricosane (Compound C27)

Compound C27 was synthesized in 86% yield according to the procedure of Example 2-3. $^1$H NMR (400 MHz, $CDCl_3$): δ 5.14 (s, 2H), 3.94 (s, 4H), 3.45 (d, J=5.6 Hz, 12H), 3.37 (t, J=2.8 Hz, 8H), 2.18-2.14 (m, 2H), 1.56-1.53 (m, 8H), 1.33-1.31 (m, 16H), 0.89 (t, J=6.6 Hz, 6H); $^{13}$CNMR (100 MHz, $CDCl_3$): δ 143.2, 113.2, 71.8, 71.3, 69.2, 68.9, 40.4, 29.5, 28.5, 22.6, 14.1.

<5-4> Synthesis of 3-(3-(pentyloxy)-2-((pentyloxy)methyl)propoxy)-2-((3-(pentyloxy)-2-((pentyloxy)methyl)propoxy)methyl) propan-1-ol (Compound D30)

Compound D30 was synthesized in 76% yield according to the procedure of Example 2-4. $^1$H NMR (400 MHz, $CDCl_3$): δ 3.73 (d, J=2.8 Hz, 2H), 3.55-3.49 (m, 4H), 3.46 (d, J=5.6 Hz, 4H), 3.42 (d, J=6.0 Hz, 8H), 3.38 (t, J=2.8 Hz, 8H), 2.92 (br s, 1H) 2.17-2.09 (m, 3H), 1.58-1.52 (quin, J=6.8 Hz, 8H), 1.33-1.30 (m, 16H), 0.89 (t, J=6.8 Hz, 12H); $^{13}$CNMR (100 MHz, $CDCl_3$): δ 71.4, 70.1, 69.3, 64.4, 41.4, 40.4, 29.4, 28.5, 22.6, 14.2.

<5-5> Synthesis of 2-(hydroxymethyl)-2-((3-(3-(pentyloxy)-2-((pentyloxy)methyl) propoxy)-2-((3-(pentyloxy)-2-((pentyloxy)meth-yl)propoxy)methyl) propoxy) methyl)propane-1,3-diol (Compound E33)

Compound E33 was synthesized in 44% yield according to the procedure of Example 2-5. $^1$H NMR (400 MHz, $CDCl_3$): δ 3.65 (s, 6H), 3.48-3.37 (m, 28H), 2.16-2.10 (m, 3H), 1.59-1.52 (quin, J=6.8 Hz, 8H), 1.35-1.30 (m, 16H), 0.90 (t, J=6.8 Hz, 12H); $^{13}$CNMR (100 MHz, $CDCl_3$): δ 72.8, 71.4, 70.3, 69.8, 69.6, 69.2, 64.4, 45.2, 40.3, 40.1, 29.4, 28.4, 22.6, 14.2.

<5-6> Synthesis of DTM-E5a

DTM-E5a was synthesized in 62% yield according to the general maltosylation procedure of Example 2-6. $^1$H NMR (400 MHz, $CDCl_3$): δ 8.09 (d, J=8.0 Hz, 6H), 7.98 (d, J=8.0 Hz, 6H), 7.87 (t, J=8.0 Hz, 20H), 7.79 (d, J=8.0 Hz, 6H), 7.68 (d, J=8.0 Hz, 6H), 7.54-7.18 (m, 61H), 6.12 (t, J=10.0 Hz, 3H), 5.67 (t, J=6.8 Hz, 6H), 5.45 (t, J=9.6 Hz, 3H), 5.19 (dd, J=10.4 Hz, J=4 Hz, 3H), 5.14 (t, J=8.0 Hz, 3H), 4.61 (t, J=12.0 Hz, 6H), 4.36-4.28 (m, 10H), 4.18 (d, J=8.0 Hz, 3H), 3.74 (d, J=8.0 Hz, 3H), 3.68 (d, J=12.0 Hz, 3H), 3.40-3.35 (m, 16H), 3.31-3.29 (m, 3H), 3.22-3.14 (m, 9H), 3.01 (d, J=8.0 Hz, 3H), 2.15-2.12 (m, 2H), 1.95-1.89 (m, 1H), 1.54-1.53 (m, 8H), 1.31-1.29 (m, 16H), 0.88 (t, J=7.2 Hz, 12H); $^{13}$CNMR (100 MHz, $CDCl_3$): δ 165.6, 165.1, 165.0, 164.8, 133.7, 133.5, 133.2, 130.0, 129.9, 129.8, 129.7, 129.5, 129.4, 129.0, 128.9, 128.8, 128.7, 128.5, 128.3, 100.9, 95.9, 74.8, 72.3, 72.2, 71.3, 69.9, 69.7, 69.3, 69.0, 68.9, 63.5, 62.4, 60.5, 44.9, 40.4, 29.5, 28.5, 22.6, 22.1, 14.2.

<5-7> Synthesis of DTM-E5

DTM-E5 was synthesized according to the general deprotection procedure of Example 2-7. $^1$H NMR (400 MHz, $CD_3OD$): δ 5.15 (d, J=4.0 Hz, 3H), 4.34 (d, J=8.0 Hz, 3H), 3.96 (d, J=12.0 Hz, 3H), 3.90-3.79 (m, 10H), 3.68-3.59 (m, 18H), 3.53 (t, J=10.0 Hz, 6H), 3.45-3.40 (m, 27H), 3.27 (t, J=8.0 Hz, 6H), 2.15-2.08 (m, 3H), 1.56 (quin, J=6.8 Hz, 8H), 1.35-1.32 (m, 16H), 0.92 (t, J=7.0 Hz, 12H); $^{13}$CNMR (100 MHz, CD$_3$OD): δ 105.1, 103.1, 81.5, 77.9, 76.6, 75.2, 74.9, 74.3, 72.4, 71.5, 71.2, 70.8, 70.3, 70.0, 62.8, 62.3, 46.7, 41.8, 30.6, 29.7, 23.7, 14.7. HRMS (FAB$^+$): calcd. for C$_{73}$H$_{136}$O$_{40}$ [M+Na]$^+$ 1675.8506, found 1675.8510.

<Preparation Example 6> Synthesis of DTM-E6

<6-1> Synthesis of 1-((2-((hexyloxy)methyl)allyl)oxy)hexane (Compound A22)

Compound A22 was synthesized in 92% yield according to the procedure of Example 2-1. $^1$H NMR (400 MHz, CDCl$_3$): δ 5.01 (s, 2H), 3.82 (s, 4H), 3.27 (t, J=9.6 Hz, 4H), 1.48-1.41 (m, 4H), 1.23-1.17 (m, 12H), 0.76 (t, J=5.8 Hz, 6H); $^{13}$CNMR (100 MHz, CDCl$_3$): δ 143.3, 112.9, 71.4, 70.4, 31.7, 29.7, 25.9, 22.6, 13.9.

<6-2> Synthesis of 3-(pentyloxy)-2-((pentyloxy)methyl)propan-1-ol (Compound B25)

Compound B25 was synthesized in 90% yield according to the procedure of Example 2-2. $^1$H NMR (400 MHz, CDCl$_3$): δ 3.75 (d, J=4.8 Hz, 2H), 3.52 (m, 4H), 3.41 (t, J=6.6 Hz, 4H), 3.04 (br s, 1H), 2.09 (m, 1H), 1.60-1.53 (m, 4H), 1.33-1.28 (m, 12H), 0.88 (t, J=6.8 Hz, 6H); $^{13}$CNMR (100 MHz, CDCl$_3$): δ 71.1, 69.9, 62.6, 41.4, 31.4, 29.4, 25.6, 22.4, 13.7.

<6-3> Synthesis of 9,17-bis((hexyloxy)methyl)-13-methylene-7,11,15,19-tetraoxapentacosane (Compound C28)

Compound C28 was synthesized in 85% yield according to the procedure of Example 2-3. $^1$H NMR (400 MHz, CDCl$_3$): δ 5.13 (s, 2H), 3.94 (s, 4H), 3.44 (d, J=3.6 Hz, 12H), 3.38 (t, J=6.4 Hz, 8H), 2.18-2.12 (m, 2H), 1.62-1.43 (m, 8H), 1.38-1.21 (m, 24H), 0.89 (t, J=6.6 Hz, 6H); $^{13}$CNMR (100 MHz, CDCl$_3$): δ 143.2, 113.2, 71.8, 71.3, 69.2, 68.9, 40.5, 31.8, 29.8, 25.9, 22.8, 14.1.

<6-4> Synthesis of 3-(3-(hexyloxy)-2-((hexyloxy)methyl)propoxy)-2-((3-(hexyloxy)-2-((hexyloxy)methyl)propoxy)methyl) propan-1-ol (Compound D31)

Compound D31 was synthesized in 74% yield according to the procedure of Example 2-4. $^1$H NMR (400 MHz, CDCl$_3$): δ 3.71 (d, J=4.8 Hz, 2H), 3.55-3.45 (m, 8H), 3.42 (d, J=6.4 Hz, 8H), 3.38 (t, J=6.6 Hz, 8H), 3.07 (br s, 1H), 2.16-2.08 (m, 2H), 1.58-1.50 (quin, J=6.8 Hz, 8H), 1.33-1.20 (m, 24H), 0.88 (t, J=6.8 Hz, 12H); $^{13}$CNMR (100 MHz, CDCl$_3$): δ 71.3, 71.0, 69.9, 69.2, 64.0, 41.4, 40.3, 31.7, 29.6, 25.8, 22.6, 14.1.

<6-5> Synthesis of 2-((3-(3-(hexyloxy)-2-((hexyloxy)methyl)propoxy)-2-((3-(hexyloxy)-2-((hexyloxy)methyl)propoxy)methyl)propoxy)methyl)-2-(hydroxymethyl)propane-1,3-diol (Compound E34)

Compound E34 was synthesized in 42% yield according to the procedure of Example 2-5. $^1$H NMR (400 MHz, CDCl$_3$): δ 3.66 (s, 6H), 3.50-3.48 (m, 4H), 3.43-3.37 (m, 24H), 3.08 (br s, 3H), 2.15-2.12 (m, 3H), 1.54-1.53 (m, 8H), 1.31-1.29 (m, 24H), 0.88 (t, J=7.2 Hz, 12H); $^{13}$CNMR (100 MHz, CDCl$_3$): δ 73.0, 71.5, 70.4, 69.9, 69.7, 69.3, 65.0, 45.1, 40.3, 31.9, 29.8, 26.0, 22.8, 14.3.

<6-6> Synthesis of DTM-E6a

DTM-E6a was synthesized in 65% yield according to the general maltosylation procedure of Example 2-6. $^1$H NMR (400 MHz, CDCl$_3$): δ 8.10 (d, J=8.0 Hz, 6H), 7.98 (d, J=8.0 Hz, 6H), 7.88 (t, J=8.0 Hz, 20H), 7.79 (d, J=6.0 Hz, 6H), 7.68 (d, J=8.0 Hz, 6H), 7.54-7.19 (m, 61H), 6.14 (t, J=9.8 Hz, 3H), 5.68 (t, J=9.6 Hz, 6H), 5.47 (t, J=9.2 Hz, 3H), 5.21 (dd, J=10.4 Hz, J=3.2 Hz, 3H), 5.16 (t, J=8.8 Hz, 3H), 4.59 (t, J=12.0 Hz, 6H), 4.38-4.29 (m, 9H), 4.20 (d, J=10.4 Hz, 3H), 3.75 (d, J=7.2 Hz, 3H), 3.69 (d, J=12.0 Hz, 3H), 3.39-3.30 (m, 17H), 3.21-3.19 (m, 9H), 3.13-3.05 (m, 3H), 3.02 (d, J=8.4 Hz, 3H), 2.15-2.08 (m, 2H), 1.95-1.88 (m, 1H), 1.54-1.52 (m, 8H), 1.31-1.29 (m, 24H), 0.87 (t, J=4.0 Hz, 12H); $^{13}$CNMR (100 MHz, CDCl$_3$): δ 166.1, 165.8, 165.6, 165.1, 164.8, 133.7, 133.5, 133.2, 129.9, 129.8, 129.7, 129.5, 129.4, 129.0, 128.9, 128.8, 128.7, 128.5, 128.3, 100.9, 95.9, 74.8, 72.5, 72.3, 71.3, 70.2, 69.9, 69.8, 69.2, 69.0, 68.9, 63.5, 62.4, 44.9, 40.4, 31.8, 29.7, 25.9, 22.7, 14.2.

<6-7> Synthesis of DTM-E6

DTM-E6 was synthesized according to the general deprotection procedure of Example 2-7. $^1$H NMR (400 MHz, CD$_3$OD): δ 5.17 (d, J=4.0 Hz, 3H), 4.35 (d, J=8.0 Hz, 3H), 3.96 (d, J=9.6 Hz, 3H), 3.90-3.81 (m, 10H), 3.69-3.60 (m, 18H), 3.53 (t, J=12.0 Hz, 6H), 3.45-3.41 (m, 27H), 3.35-3.24 (m, 6H), 2.05-1.99 (m, 3H), 1.56 (quin, J=6.6 Hz, 8H), 1.35-1.32 (m, 24H), 0.92 (t, J=7.0 Hz, 12H); $^{13}$CNMR (100 MHz, CD$_3$OD): δ 105.0, 102.9, 81.4, 77.8, 76.5, 75.1, 74.8, 74.1, 72.4, 71.5, 71.2, 70.7, 70.6, 70.2, 70.0, 62.8, 62.3, 46.7, 41.7, 41.6, 32.9, 30.8, 27.1, 23.8, 14.6. HRMS (FAB$^+$): calcd. for C$_{77}$H$_{144}$O$_{40}$ [M+Na]$^+$ 1732.9132, found 1731.9124.

<Preparation Example 7> Synthesis of DTM-E7

<7-1> Synthesis of 1-((2-((heptyloxy)methyl)allyl)oxy)heptane (Compound A23)

Compound A23 was synthesized in 90% yield according to the procedure of Example 2-1. $^1$H NMR (400 MHz, CDCl$_3$): δ 5.14 (s, 2H), 3.95 (s, 4H), 3.39 (t, J=6.6 Hz, 4H), 1.57 (quin, J=6.8 Hz, 4H), 1.30-1.28 (m, 16H), 0.88 (t, J=6.8 Hz, 6H); $^{13}$CNMR (100 MHz, CDCl$_3$): δ 143.4, 112.9, 71.4, 70.4, 31.9, 29.8, 29.2, 26.2, 22.6, 14.0.

<7-2> Synthesis of 3-(heptyloxy)-2-((heptyloxy)methyl)propan-1-ol (Compound B26)

Compound B26 was synthesized in 86% yield according to the procedure of Example 2-2. $^1$H NMR (400 MHz, CDCl$_3$): δ 5.14 (s, 2H), 3.94 (s, 4H), 3.45 (d, J=5.6 Hz, 12H), 3.37 (t, J=2.8 Hz, 8H), 2.18-2.14 (m, 2H), 1.56-1.53 (m, 8H), 1.33-1.31 (m, 16H), 0.89 (t, J=6.6 Hz, 6H); $^{13}$CNMR (100 MHz, CDCl$_3$): δ 143.2, 113.2, 71.8, 71.3, 69.2, 68.9, 40.4, 29.5, 28.5, 22.6, 14.1.

<7-3> Synthesis of 10,18-bis((heptyloxy)methyl)-14-methylene-8,12,16,20-tetraoxaheptacosane (Compound C29)

Compound C29 was synthesized in 85% yield according to the procedure of Example 2-3. $^1$H NMR (400 MHz, CDCl$_3$): δ 5.13 (s, 2H), 3.94 (s, 4H), 3.45 (d, J=3.6 Hz, 12H), 3.38 (t, J=6.4 Hz, 8H), 2.18-2.12 (m, 2H), 1.57-1.51 (m, 8H), 1.30-1.28 (m, 32H), 0.88 (t, J=6.6 Hz, 6H); 13CNMR (100 MHz, CDCl$_3$): δ 143.3, 113.2, 71.8, 71.3, 69.2, 68.9, 40.5, 31.9, 29.8, 29.3, 26.3, 22.8, 14.2.

<7-4> Synthesis of 3-(3-(heptyloxy)-2-((heptyloxy) methyl)propoxy)-2-((3-(heptyloxy)-2-((heptyloxy) methyl)propoxy)methyl) propan-1-ol (Compound D32)

Compound D32 was synthesized in 74% yield according to the procedure of Example 2-4. $^1$H NMR (400 MHz, CDCl$_3$): δ 3.72 (d, J=4.8 Hz, 2H), 3.54-3.49 (m, 4H), 3.46 (d, J=6.0 Hz, 4H), 3.41 (d, J=6.0 Hz, 8H), 3.38 (t, J=6.4 Hz, 8H), 2.93 (br s, 1H), 2.15-2.10 (quin, J=6.0 Hz, 2H), 1.56-1.52 (m, 8H), 1.33-1.20 (m, 32H), 0.88 (t, J=5.2 Hz, 12H); $^{13}$CNMR (100 MHz, CDCl$_3$): δ 71.3, 70.8, 69.3, 64.3, 63.9, 41.4, 40.3, 31.9, 29.7, 29.2, 26.2, 22.7, 14.2.

<7-5> Synthesis of 2-((3-(3-(heptyloxy)-2-((heptyloxy)methyl)propoxy)-2-((3-(heptyloxy)-2-((heptyloxy)methyl)propoxy)methyl)-propoxy)methyl)-2-(hydroxymethyl)propane-1,3-diol (Compound E35)

Compound E35 was synthesized in 44% yield according to the procedure of Example 2-5. $^1$H NMR (400 MHz, CDCl$_3$): δ 3.66 (s, 6H), 3.42-3.39 (m, 8H), 3.36-3.30 (m, 20H), 3.08 (br s, 3H), 2.15-2.12 (m, 3H), 1.49-1.46 (m, 8H), 1.31-1.29 (m, 32H), 0.81 (t, J=6.8 Hz, 12H); $^{13}$CNMR (100 MHz, CDCl$_3$): δ 72.8, 71.4, 70.3, 69.8, 69.6, 69.2, 64.4, 45.1, 40.2, 40.1, 31.9, 29.7, 29.3, 26.2, 22.7, 14.2.

<7-6> Synthesis of DTM-E7a

DTM-E7a was synthesized in 66% yield according to the general maltosylation procedure of Example 2-6. $^1$H NMR (400 MHz, CDCl$_3$): δ 8.10 (d, J=8.0 Hz, 6H), 7.98 (d, J=8.0 Hz, 6H), 7.88 (t, J=8.0 Hz, 20H) 7.79 (d, J=6.0 Hz, 6H), 7.68 (d, J=8.0 Hz, 6H), 7.56-7.18 (m, 61H), 6.13 (t, J=10.0 Hz, 3H), 5.68 (t, J=10.0 Hz, 6H), 5.46 (t, J=10.0 Hz, 3H), 5.20 (dd, J=8 Hz, J=4 Hz, 3H), 5.15 (t, J=8.0 Hz, 3H), 4.59 (t, J=10.0 Hz, 6H), 4.37-4.29 (m, 10H), 4.19 (d, J=12.0 Hz, 3H), 3.75 (d, J=8.0 Hz, 3H), 3.69 (d, J=8.0 Hz, 3H), 3.39-3.30 (m, 16H), 3.30-3.27 (m, 3H), 3.21-3.15 (m, 6H), 3.12-3.06 (m, 3H), 3.02 (d, J=12.0 Hz, 3H), 2.15-2.08 (m, 2H), 1.95-1.88 (m, 1H), 1.54-1.52 (m, 8H), 1.31-1.29 (m, 32H), 0.87 (t, J=4.0 Hz, 12H); $^{13}$CNMR (100 MHz, CDCl$_3$): δ 166.1, 165.8, 165.6, 165.1, 164.8, 133.5, 133.2, 129.9, 129.8, 129.7, 129.5, 129.4, 129.0, 128.9, 128.8, 128.7, 128.5, 128.3, 100.9, 95.9, 74.8, 72.3, 72.2, 71.3, 69.9, 69.8, 69.3, 69.0, 67.8, 63.5, 62.4, 44.9, 40.4, 31.9, 29.3, 26.3, 22.7, 14.2.

<7-7> Synthesis of DTM-E7

DTM-E7 was synthesized according to the general deprotection procedure of Example 2-7. $^1$H NMR (400 MHz, CD3OD): δ 5.15 (d, J=4.0 Hz, 3H), 4.34 (d, J=8.0 Hz, 3H), 3.97 (d, J=12.0 Hz, 3H), 3.88 (d, J=12.0 Hz, 4H), 3.83-3.78 (m, 6H), 3.68-3.61 (m, 18H), 3.55 (t, J=16.0 Hz, 6H), 3.46-3.30 (m, 27H), 3.27 (m, 6H), 2.05-1.99 (m, 3H), 1.56 (quin, J=6.6 Hz, 2H), 1.33-1.31 (m, 32H), 0.90 (t, J=6.6 Hz, 12H); $^{13}$CNMR (100 MHz, CD3OD): δ 105.1, 103.1, 81.5, 77.9, 76.6, 75.2, 74.9, 74.3, 72.4, 71.6, 70.8, 70.7, 70.3, 70.1, 62.8, 62.3, 41.8, 33.2, 30.9, 30.4, 27.5, 23.8, 14.7s. HRMS (FAB$^+$): calcd. for C$_{81}$H$_{152}$O$_{40}$ [M+Na]$^+$ 1787.9758, found 1787.9763.

<Example 3> Properties of DTMs

To identify the properties of DTMs synthesized according to the synthetic methods of Examples 1 and 2, the molecular weights (M.W.) and critical micellar concentrations (CMCs) of DTMs, and hydrodynamic radii ($R_h$) of formed micelles were measured.

Specifically, the CMCs were measured using hydrophobic fluorescence staining and diphenylhexatriene (DPH), and the hydrodynamic radii ($R_h$) of the micelles formed by each formulation were measured by dynamic light scattering (DLS). The results were compared with that of a conventional amphiphilic molecule (detergent), that is, DDM, and are shown in Table 1.

TABLE 1

| Detergent | M. W.[a] | CMC (M) | CMC (wt %) | R$_2$ (nm)[b] |
|---|---|---|---|---|
| DTM-A5 | 1485.7 | ~20 | ~0.0030 | 3.6 ± 0.1 |
| DTM-A6 | 1541.8 | ~10 | ~0.0015 | 3.7 ± 0.0 |
| DTM-A7 | 1598.0 | ~5 | ~0.0008 | 18.2 ± 0.5 |
| DTM-A8 | 1654.1 | ~3 | ~0.0005 | 34.0 ± 0.4 |
| DTM-E5 | 1653.8 | ~40 | ~0.0070 | 3.4 ± 0.2 |
| DTM-E6 | 1709.9 | ~10 | ~0.0017 | 3.9 ± 0.0 |
| DTM-E7 | 1766.1 | ~5 | ~0.0009 | 16.2 ± 0.7 |
| DDM | 510.1 | 170 | 0.0087 | 3.4 ± 0.0 |

[a]Molecular weight of detergents.
[b]Detergent hydrodynamic radius measured at 0.5 wt % detergent concentration by dynamic light scattering (DLS).

The CMC values of DTMs were much smaller than that of DDM. It was seen that the CMC values decrease as the length of an alkyl chain increases in both types of DTMs. This means that the longer the alkyl chain, the stronger the hydrophobic interaction between amphiphilic compounds. Therefore, since DTMs more easily form micelles at lower concentrations, it can be seen that DTMs tend to highly agglomerate in an aqueous solution, compared to DDM.

The sizes of the micelles formed by DTMs ranged from 3.2 to 34.4 nm, indicating that larger micelles are formed, compared to DDM. The sizes of the micelles formed by DTMs increased as the alkyl chain lengths increased. In addition, as a result of analyzing the size distribution of the micelles formed by DTMs, it was confirmed that most DTMs except DTM-A7 and DTM-A8 form micelles with uniform sizes (FIG. 4).

<Example 4> Evaluation of Stabilization Ability of DTMs on *R. capsulatus* Super Assembly (LHI-RC) Structure (FIG. 5)

An experiment was conducted to evaluate the stabilization ability of DTMs on LHI-RC. The photosynthetic super assembly consists of a complex of light-harvesting complex I (LHI) and a reaction center (RC). The structural stability of LHI-RC was measured by a method of monitoring the structure of a protein for 20 days using UV-Vis spectroscopy. LHI-RC protein stability according to the concentration of an amphiphilic molecule was investigated using all DTMs of the present invention, and conventional amphiphilic molecules, such as DDM and OG, and the concentrations of an amphiphilic molecule used here were CMC+ 0.04 wt % (FIG. 5*a*) and CMC+ 0.2 wt % (FIG. 5*b*).

Specifically, LHI-RC stability was measured using a method disclosed in the paper published in 2008 by the inventors (P. S. Chae et al., *ChemBioChem* 2008, 9, 1706-1709.). Briefly, the inventors used the membrane obtained from *R. capsulatus*, U43 [pUHTM86Bgl] which does not have light-harvesting complex II (LHII). A 10 mL aliquot of the solution of the frozen *R. capsulatus* membrane was homogenized using a glass homogenizer, and incubated with gentle stirring at 32° C. for 30 minutes. The homogenized membrane was treated with 1.0 wt % DDM for 30 minutes at 32° C. Membrane debris was subjected to ultracentrifugation for 30 minutes at 4° C. and 315,000 g, resulting in the collection of a pellet. 200 μL of $Ni^{2+}$-NTA resin (pre-equilibrated and stored in a buffer containing 10 mM Tris, pH 7.8) was added to a supernatant containing the LHI-RC complex solubilized in DDM, and incubated at 4° C. for 1 hour. The resin-containing solution was filtrated using 10 HisSpinTrap columns, and each column was washed twice with a 500 μL binding buffer containing 10 mM Tris (pH 7.8), 100 mL NaCl and 1×CMC DDM. Following the replacement with a new ultracentrifuge tube, the LHI-RC complex purified by DDM was eluted using a buffer containing 1M imidazole (2×300 μL). 80 μL of the protein sample was diluted with 920 μL of each of DTM-As, DTM-Es, DDM and OG so that the final concentration was CMC+ 0.04 wt % or CMC+ 0.2 wt %. The LHI-RC complex produced in each detergent was incubated for 15 days at 25° C. Protein stability was measured at regular intervals during the incubation by measuring UV-Vis spectra of the samples in the range of 650 to 950 nm. Protein integrity was evaluated by monitoring absorbance ($A_{875}$) at 875 nm.

All DTMs were superior to DDM and OG in terms of complex stability. Among DTMs, DTM-E5 showed the most excellent effect, but most DTMs showed similar performance. When the concentration of each compound increases from CMC+ 0.04 wt % to CMC+ 0.2 wt %, protein stability decreases in both DDM and OG (FIG. 5). Among DTMs, although DTM-E7 obtained a similar result, the other DTMs showed an excellent effect of stabilizing the LHI-RC complex at a higher (CMC+ 0.2 wt %) (FIG. 5).

<Example 5> Evaluation of Ability of DTMs to Stabilize Membrane Protein (LeuT) Structure An experiment was conducted to measure the structural stability of a LeuT protein by DTMs. A LeuT protein activation degree was measured by SPA using a protein substrate ([3H]-Leu), and concentrations of DTMs or DDM were CMC+ 0.04 wt % and CMC+ 0.2 wt %.

Wild-type LeuT derived from *Aquifex aeolicus* was purified according to the method disclosed in the paper written by G. Deckert et al. (*Nature* 1998, 392, 353-358.). LeuT is expressed in *E. coli* C41(DE3) transformed with pET16b encoding a C-terminal 8×His-tagged transporter (the expression plasmid was provided by Dr E. Gouaux, Vollum Institute, Portland, Oreg., USA). Briefly, a LeuT protein was isolated and solubilized in 1.0 wt % DDM, and then the protein was bound to $Ni^{2+}$-NTA resin (Life Technologies, Denmark), followed by elution with 20 mM Tris-HCl (pH 8.0), 1 mM NaCl, 199 mM KCl, 0.05% DDM and 300 mM imidazole. Afterward, approximately 1.5 mg/ml of a protein sample (stock) was diluted 10-fold with an identical buffer which does not include DDM or imidazole, but is supplemented with each of DTMs or DDM (control) to obtain a final concentration of CMC+ 0.04 wt % or CMC+ 0.2 wt %. The protein sample was stored for 12 days at room temperature, and then centrifuged at regular intervals during the incubation prior to the measurement of protein activity. Protein activity was determined by measuring [$^3$H]-Leu binding using SPA (M. Quick et al., *Proc. Natl, Acad. Sci. U.S.A.* 2007, 104, 3603-3608.). The assay was performed on 5 μL of each protein sample in a buffer containing 200 mM NaCl and each compound at the final concentration. In the presence of 20 nM [$^3$H]-Leu and copper chelate (His-Tag) YSi beads (both purchased from PerkinElmer, Denmark), a SPA reaction was performed. [$^3$H]-Leu binding was measured using a MicroBeta liquid scintillation counter (PerkinElmer).

As shown in FIGS. 6 and 7, compared to DDM, all DTMs except DTM-A6 having the longest alkyl chain showed an excellent ability to maintain the activity of solubilized LeuT. The result was similar when the concentration of the amphiphilic compound was increased from CMC+ 0.04 wt % to CMC+ 0.2 wt %.

<Example 6> Evaluation of Ability of DTMs to Stabilize MelB Membrane Protein Structure An experiment was conducted to measure the structural stability of a *Salmonella typhimurium* melibiose permease (MelB) protein by DTMs.

Specifically, *Salmonella typhimurium* MelB$_{St}$ (melibiose permease) having a 10-His tag at the C-terminus was expressed in *E. coli* DW2 cells (ΔmelB and ΔlacZY) using a pK95ΔAHB/WT MelB$_{St}$/CH10 plasmid. Cell growth and membrane preparation were carried out according to the methods disclosed in the paper written by A. S. Ethayathulla et al. (*Nat. Commun.* 2014, 5, 3009). A protein assay was performed using a Micro BCA kit (Thermo Scientific, Rockford, Ill.). MelB$_{St}$ stability in DTMs or DDM was evaluated using the protocol disclosed in *Nat. Methods* 2010, 7, 1003-1008, written by P. S. Chae et al. A MelB$_{St}$-containing membrane sample (the final protein concentration was 10 mg/mL) was incubated in a solubilization buffer containing 1.5% (w/v) DDM or DTM (20 mM sodium phosphate, pH 7.5, 200 mM NaCl, 10% glycerol and 20 mM melibiose) at four different temperatures (0, 45, 55 and 65° C.) for 90 minutes. To remove an insoluble material, ultracentrifugation was performed using a Beckman Optima™ MAX ultracentrifuge equipped with a TLA-100 rotor at 355,590 g and 4° C. for 45 minutes. 20 μg of the membrane protein which did not undergo ultracentrifugation was applied to an untreated membrane or the same amount of extracts of the compounds after ultracentrifugation, and the treated samples were loaded in respective wells at an equal volume. The loaded samples were analyzed by SDS-15% PAGE, and then visualized by immunoblotting with a Penta-His-HRP antibody (Qiagen, Germantown, Md.).

In addition, RSO vesicles were prepared to be used for Trp→D$^2$G FRET assay. The RSO membrane vesicles were prepared by osmotic lysis from *E. coli* DW2 cells containing MelB$_{St}$ or MelB$_{Ec}$. The RSO membrane vesicles mixed in a buffer (pH 7.5) containing 100 mM KPi and 100 mM NaCl at a protein concentration of 1 mg/ml were treated with 1.0% individual compounds (DDM, DTM-A5 and DTM-A6) for 60 minutes at 23° C., and ultracentrifuged using a TLA 120.2 rotor at 300,000 g or more for 45 minutes at 4° C. Supernatants were applied to a FRET (Trp→D$^2$G) experiment using an Amico-Bowman Series 2 (AB2) spectrofluorometer. The 2'-(N-dansyl)aminoalkyl-1-thio-β-D-galactopyranoside (D$^2$G, dansyl-galactoside) was obtained from Drs. Gerard Leblanc and H. Ronald Kaback. D$^2$G FRET signals of MelB$_{St}$ and MelB$_{Ec}$ were collected at 490 and 465 nm, respectively, upon excitation of Trp residues at 290 nm. 10 μM D$^2$G and excess melibiose or an equal amount of water (control) was added into an MelB solution at the time points of 1 minute and 2 minutes, respectively.

As shown in FIGS. 8a and 8b, DDM stably solubilized MelB$_{st}$ at 0° C. and 45° C. Most DTMs except DTM-E6 had similar or lower efficiency of solubilizing the protein from the membrane at 0° C. and 45° C., compared to DDM. However, when a temperature was increased to 55° C., DTM-A5 and DTM-A6 among DTMs most effectively solubilized the MelB$_{st}$ protein. At 65° C., the solubilization of the MelB$_{st}$ protein did not occur by DDM and DTMs.

Overall, at a low temperature (0° C.), DDM showed a higher protein extraction efficiency than DTMs, whereas at a relatively high temperature (45° C.), the protein extraction efficiency of DTMs increased, and DTM-E6, DTM-A5 and DTM-A6 showed similar efficiency to DDM. At a higher temperature (55° C.), most DTMs showed higher efficiency than DDM, confirming that DTMs are superior to DDM in terms of protein solubilization stability according to temperature.

As shown in FIG. 8c, only one of the two homologs of the MelB protein solubilized in DDM maintains protein function, but all homologs of the MelB protein solubilized in DTM-A5 and DTM-A6 maintain protein function. Thus, it was confirmed that DTM-A5 and DTM-A6 are not only effective in solubilization of MelB proteins, but also superior in maintaining protein function, compared to DDM.

<Example 7> Evaluation of Ability of DTMs to Stabilize β$_2$AR Protein

<7-1> Measurement of Long-Term Stability

A receptor was expressed in Sf9 insect cells infected with a baculovirus and solubilized in 1% DDM. The DDM-solubilized receptor was purified by alprenolol-sepharose in the presence of 0.01% cholesteryl succinate (CHS). β$_2$AR purified by DDM was diluted with a buffer containing DDM or DTM (DTM-A6, DTM-A7 or DTM-E7) to reach the final concentration of CMC+0.2 wt %. β$_2$AR solubilized in each compound was stored for 4 days at room temperature, and the ligand binding ability of the receptor was measured at regular intervals by incubating the receptor with 10 nM radioactive [$^3$H]-dihydroalprenolol (DHA) for 30 minutes at room temperature. The mixture was loaded into a G-50 column, and a supernatant was collected using a certain amount of binding buffer (supplemented with 20 mM HEPES pH 7.5, 100 mM NaCl, 0.5 mg/ml BSA). In addition, a 15 ml scintillation fluid was added. Receptor-binding [$^3$H]-DHA was measured using a scintillation counter (Beckman).

As a result, DTM-A6 and DTM-E7 among DTMs showed the ability to maintain initial activity of the solubilized receptor, which was similar to DDM (FIG. 9). However, in terms of long-term receptor stabilization ability, the receptors solubilized by DDM and DTM-E7 showed rapid loss of activity over time, and receptors solubilized in DTM-A6 and DTM-A7 showed that a receptor activity was consistently maintained during incubation for 4 days (FIG. 9a). In addition, DTM-As having a long alkyl chain generally had an excellent ability to maintain receptor protein activity, compared to DTM-Es. In addition, among DTMs, compounds having C6 and C7 alkyl chains, that is, long alkyl chains, generally had excellent efficiency, confirming that the efficacy of DTMs depends on alkyl chain length (FIG. 10). Thus, DTM-A6 and DTM-A7 are determined to be more effective in research on a solubilized receptor protein than DDM.

<7-2> Purification and Measurement of Stability of β$_2$AR-G$_s$ Complex Solubilized in DTM-A6

100 µM β$_2$AR solubilized in 0.1% DDM was mixed with 120 µM G$_s$ heterotrimer for 30 minutes at room temperature. 0.5 unit of apyrase (NEB) and 2 mM MgCl$_2$ was added to facilitate complex formation, followed by further incubation for one hour. Subsequently, 1% DTM-A6 was added such that the final concentration reached 0.8%, and the sample was further incubated for 30 minutes to change DDM to DTM-A6. The protein solution was loaded into a M1 Flag column, washed with a series of buffers with different molar ratios of 0.1% DDM buffer to 0.5% DTM-A6 buffer to completely change DDM to DTM-A6, and the protein was finally eluted with 0.05% (70×CMC) DTM-A6 buffer. Preparative gel filtration was performed to purify the β$_2$AR-G$_s$ complex with a running buffer (20 mM HEPES pH 7.5, 100 mM NaCl, 0.005% DTM-A6, 1 mM BI, 100 mM TCEP). To measure the stability of the β$_2$AR-G$_s$ complex in DTM-A6, analytical gel filtrations were performed using the running buffer as above, but after 3 and 15-day incubation, performed without DTM-A6 (compound-free condition).

As shown in FIG. 9b, it was confirmed that, in contrast to the result obtained from the β$_2$AR-G$_s$ complex purified by DDM in the previous study, the β$_2$AR-G$_s$ complex purified by DTM-A6 continuously maintains its integrity as a complex for 15 days. In the case of DDM, the complex showed significant dissociation between the receptor and G$_s$ protein even after 2 day-incubation.

<7-3> Negative Stain EM Analysis of β$_2$AR-G$_s$ Complex Solubilized in DTM-A6

A β$_2$AR-G$_s$ protein complex was prepared for electron microscopy using a conventional negative staining protocol, and imaged at room temperature using a Tecnai T12 electron microscope operated at 120 kV according to a low-dose procedure. Images were recorded at a magnification of 71,138× and a defocus value of approximately ~1.1 µm on a Gatan US4000 CCD camera. All images were binned (2×2 pixels) to obtain a pixel size of 4.16 Å at a specimen level. Particles were manually removed using e2boxer (part of the EMAN2 software suite). 2D reference-free alignment and classification of particle projections were performed using ISAC. 124,279 projections of β$_2$AR-G$_s$ were subjected to ISAC producing 131 classes consistent in two-way matching and 10,000 particle projections.

As a result, it was seen that particles generated from the β$_2$AR-G$_s$ complex purified by DTM-A6 are highly homogeneous, different from the aggregation of particles observed in the DDM-purified complex in the previous study. In addition, in representative 2D class images, individual components (β$_2$AR, G$_{\alpha s}$ and G$_{\beta \gamma}$) of the complex were clearly distinguished (FIGS. 11b and 11c). The EM images of the protein complex obtained by the use of DTM-A6 was clearer and more distinct than the images of complexes obtained using other amphiphilic molecules. This show that the amphiphilic compounds of the present invention have a significant potential to explain the structure and dynamic structural change of a membrane protein complex through EM analysis.

The invention claimed is:

1. A compound represented by Formula 1 below:

[Formula 1]

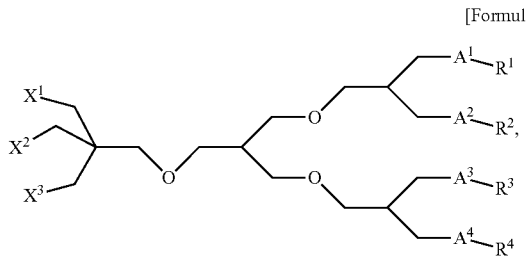

wherein $R^1$ to $R^4$ are each independently a substituted or unsubstituted $C_1$-$C_{15}$ alkyl group, a substituted or unsubstituted $C_1$-$C_{15}$ cycloalkyl group, or a substituted or unsubstituted $C_1$-$C_{15}$ aryl group; $A^1$ to $A^4$ are each independently —$CH_2$—, oxygen (O) or sulfur (S); and $X^1$ to $X^3$ are each independently an oxygen-linked saccharide.

2. The compound of claim 1, wherein the saccharide is a monosaccharide or disaccharide.

3. The compound of claim 1, wherein the saccharide is glucose or maltose.

4. The compound of claim 1, wherein $R^1$ to $R^4$ are each independently a substituted or unsubstituted $C_1$-$C_{10}$ alkyl group; $A^1$ to $A^4$ are each independently oxygen (O) or sulfur (S); and $X^1$ to $X^3$ are each independently glucose or maltose.

5. The compound of claim 1, wherein $R^1$ to $R^4$ are each independently a substituted or unsubstituted $C_1$-$C_{10}$ alkyl group; $A^1$ to $A^4$ are —$CH_2$—; and $X^1$ to $X^3$ are glucose or maltose.

6. The compound of claim 1, wherein the compound is one of Formulas 2 to 8 below:

[Formula 2]

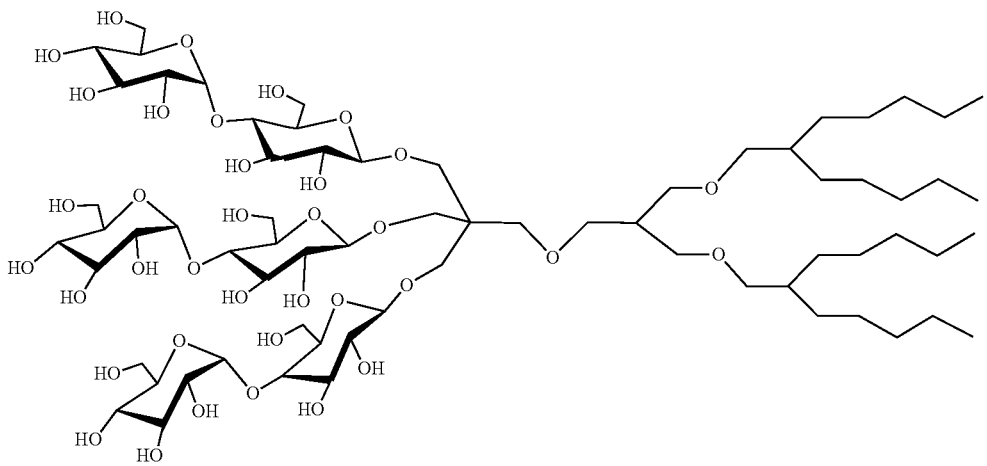

[Formula 3]

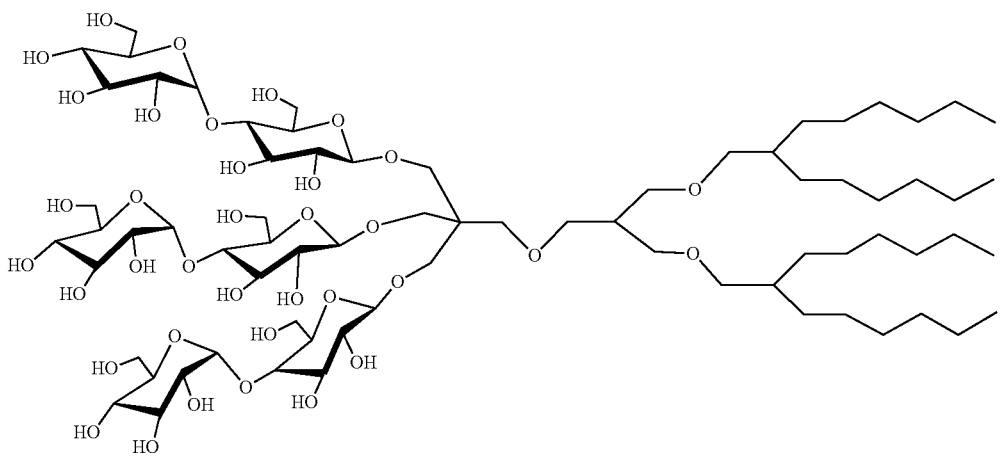

-continued
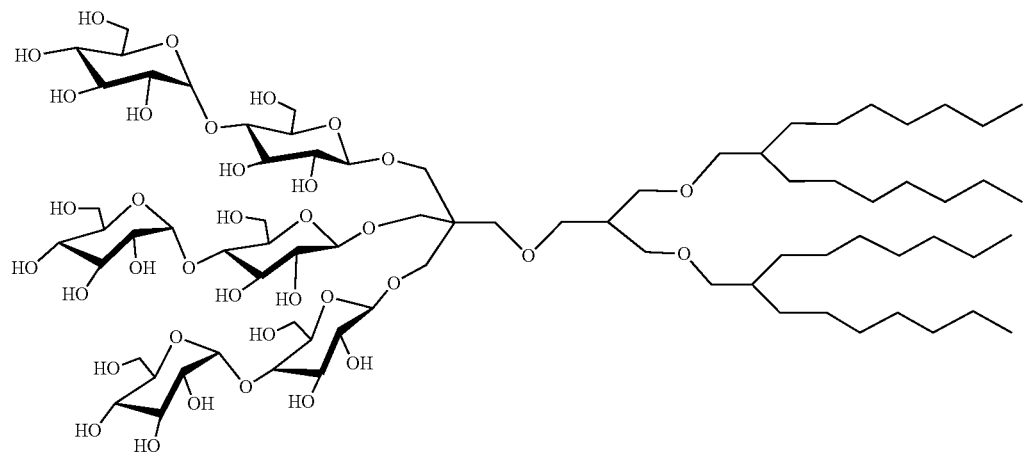
[Formula 4]
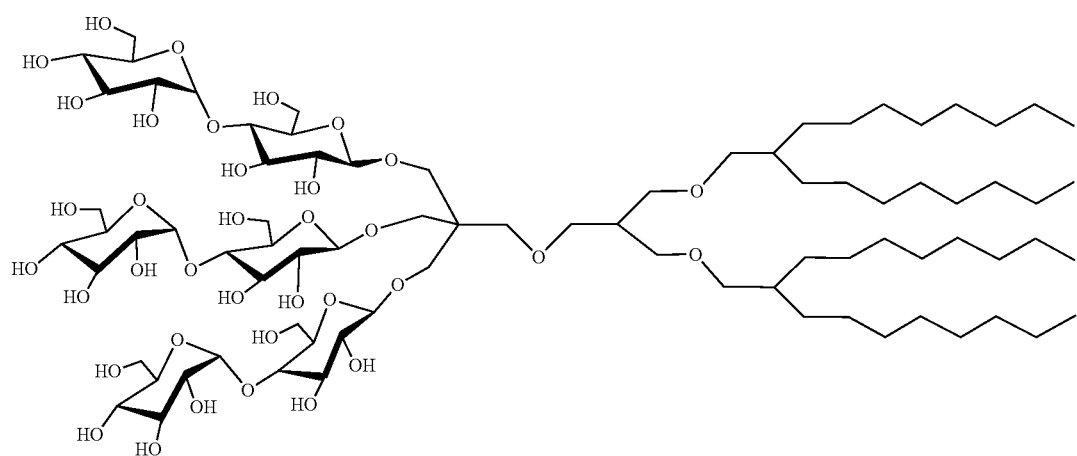
[Formula 5]
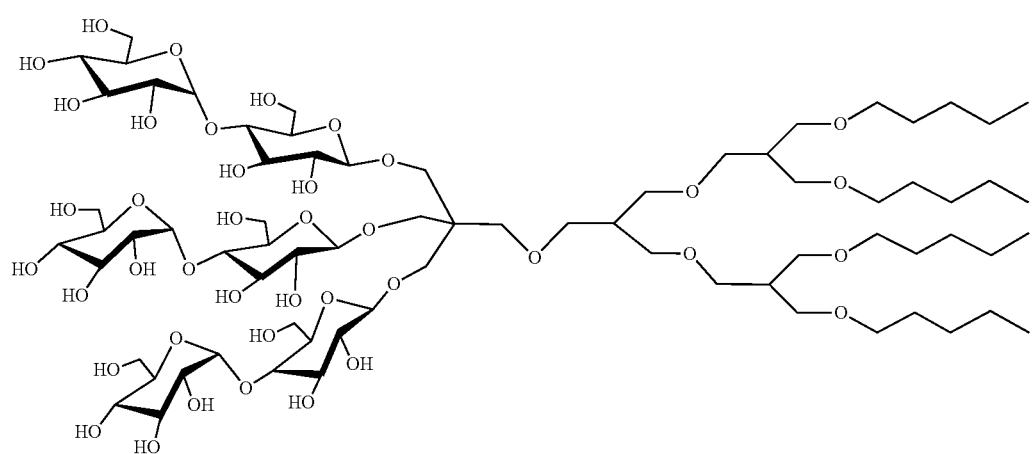
[Formula 6]

-continued

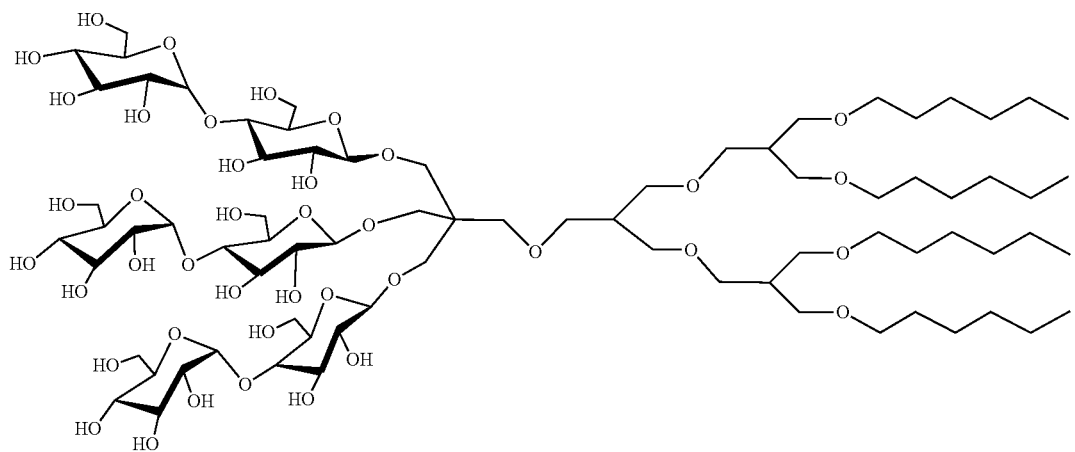

[Formula 7]

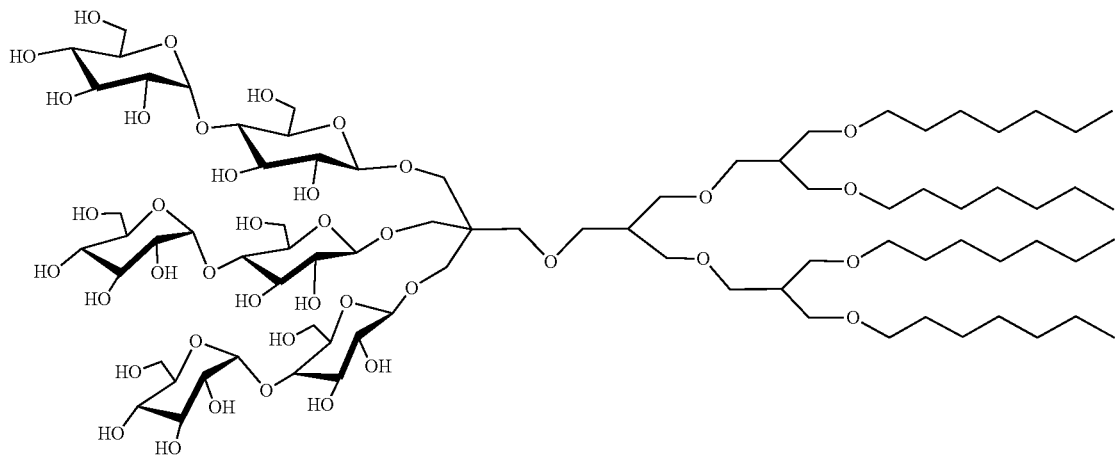

[Formula 8]

7. The compound of claim 1, wherein the compound is an amphiphilic molecule for extracting, solubilizing, stabilizing, crystallizing or analyzing a membrane protein.

8. The compound of claim 1, wherein the compound has a critical micelle concentration (CMC) of 0.0001 to 1 mM in an aqueous solution.

9. A composition for extracting, solubilizing, stabilizing, crystallizing or analyzing a membrane protein, comprising the compound of claim 1.

10. The composition of claim 9, wherein the composition is a formulation in the form of a micelle, liposome, emulsion or nanoparticle.

11. A method of preparing a compound represented by Formula 1, comprising:
   1) synthesizing a dialkylated mono-ol derivative by introducing an alkyl group to dimethylmalonate and performing reduction;
   2) synthesizing tetra-alkylated methallyl diether to which four alkyl groups are introduced by adding methallyl dichloride to the product of Step 1);
   3) synthesizing a tetra-alkylated tri-ol derivative by reacting 4-(bromomethyl)-methyl-2,6,7-trioxabicyclo[2,2,2]-octane with the product of Step 2);
   4) introducing a protecting group-attached saccharide by performing maltosylation on the product of Step 3); and
   5) performing deprotection on the product of Step 4):

[Formula 1]

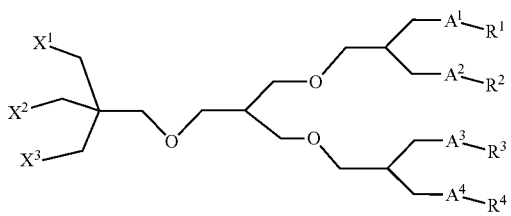

wherein $R^1$ to $R^4$ are each independently a substituted or unsubstituted $C_1$-$C_{15}$ alkyl group, a substituted or unsubstituted $C_1$-$C_{15}$ cycloalkyl group, or a substituted or unsubstituted $C_1$-$C_{15}$ aryl group; $A^1$ to $A^4$ are —$CH_2$—; and $X^1$ to $X^3$ are each independently an oxygen-linked saccharide.

12. The method of claim 11, wherein $R^1$ to $R^4$ are each independently a substituted or unsubstituted $C_1$-$C_{10}$ alkyl group; and $X^1$ to $X^3$ are maltose.

13. A method of preparing a compound represented by Formula 1 below, comprising:

1) synthesizing a dialkylated mono-ol derivative (ether-functionalized dialkylated mono-ol derivative) by reacting an aliphatic alcohol or alkylthiol with methallyl dichloride;
2) synthesizing a tetra-alkylated mono-ol derivative (ether-functionalized tetra-alkylated mono-ol derivative) by reacting methallyl dichloride with the product of Step 1);
3) synthesizing a tetra-alkylated tri-ol derivative by reacting 4-(bromomethyl)-methyl-2,6,7-trioxabicyclo[2,2,2]-octane with the product of Step 2);
4) introducing a protecting group-attached saccharide by performing maltosylation on the product of Step 3); and
5) performing deprotection on the product of Step 4):

[Formula 1]

wherein $R^1$ to $R^4$ are each independently a substituted or unsubstituted $C_1$-$C_{15}$ alkyl group, a substituted or unsubstituted $C_1$-$C_{15}$ cycloalkyl group, or a substituted or unsubstituted $C_1$-$C_{15}$ aryl group; $A^1$ to $A^4$ are each independently oxygen (O) or sulfur (S); and $X^1$ to $X^3$ are an oxygen-linked saccharide.

14. The method of claim 13, wherein $R^1$ to $R^4$ are each independently a substituted or unsubstituted $C_1$-$C_{10}$ alkyl group; and $X^1$ to $X^3$ are maltose.

15. A method of extracting, solubilizing, stabilizing, crystallizing or analyzing a membrane protein, comprising treating a membrane protein with a compound represented by Formula 1 below in an aqueous solution:

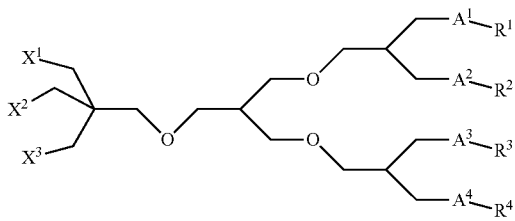

[Formula 1]

wherein $R^1$ to $R^4$ are each independently a substituted or unsubstituted $C_1$-$C_{15}$ alkyl group, a substituted or unsubstituted $C_1$-$C_{15}$ cycloalkyl group, or a substituted or unsubstituted $C_1$-$C_{15}$ aryl group; $A^1$ to $A^4$ are each independently —$CH_2$—, oxygen (O) or sulfur (S); and $X^1$ to $X^3$ are an oxygen-linked saccharide.

16. The method of claim 1, wherein $R^1$ to $R^4$ are each independently a substituted or unsubstituted $C_1$-$C_{10}$ alkyl group; $A^1$ to $A^4$ are each independently oxygen (O) or sulfur (8); and $X^1$ to $X^3$ are each independently glucose or maltose.

17. The method of claim 15, wherein $R^1$ to $R^4$ are each independently a substituted or unsubstituted $C_1$-$C_{10}$ alkyl group; $A^1$ to $A^4$ are —$CH_2$—; and $X^1$ to $X^3$ are each independently glucose or maltose.

18. The method of claim 15, wherein the membrane protein is a light harvesting-I and reaction center complex (LII-R complex), a leucine transporter (LeuT), a human $β_2$ adrenergic receptor ($β_2$AR), melibiose permease (MelB), or a combination of two or more thereof.

\* \* \* \* \*